(12) United States Patent
Sanghani et al.

(10) Patent No.: US 11,236,310 B2
(45) Date of Patent: Feb. 1, 2022

(54) PROCESS TO PREPARE ELONGATED 2-KETOACIDS AND C-5-C10 COMPOUNDS THEREFROM VIA GENETIC MODIFICATIONS TO MICROBIAL METABOLIC PATHWAYS

(71) Applicant: Dow Global Technologies LLC, Midland, MI (US)

(72) Inventors: Paresh C. Sanghani, Indianapolis, IN (US); Eric C. Shiue, Evanston, IL (US); Scott A. Greenwalt, Indianapolis, IN (US); Prakash Bhosale, Indianapolis, IN (US); Sarah Delaplane, Indianapolis, IN (US); Christopher C. Stowers, Indianapolis, IN (US)

(73) Assignee: Dow Global Technologies LLC, Midland, MI (US)

( * ) Notice: Subject to any disclaimer, the term of this patent is extended or adjusted under 35 U.S.C. 154(b) by 61 days.

(21) Appl. No.: 16/337,072

(22) PCT Filed: Dec. 30, 2016

(86) PCT No.: PCT/US2016/069476
§ 371 (c)(1),
(2) Date: Mar. 27, 2019

(87) PCT Pub. No.: WO2018/063424
PCT Pub. Date: Apr. 5, 2018

(65) Prior Publication Data
US 2019/0316158 A1    Oct. 17, 2019

Related U.S. Application Data

(60) Provisional application No. 62/402,569, filed on Sep. 30, 2016, provisional application No. 62/402,586, filed on Sep. 30, 2016.

(51) Int. Cl.
| | | |
|---|---|---|
| *C12N 9/88* | (2006.01) |
| *C12P 7/04* | (2006.01) |
| *C12N 9/10* | (2006.01) |
| *C12P 7/24* | (2006.01) |
| *C12P 7/40* | (2006.01) |
| *C12N 9/04* | (2006.01) |
| *C12P 7/44* | (2006.01) |
| *C12N 15/52* | (2006.01) |
| *C12N 9/02* | (2006.01) |
| *C12P 5/02* | (2006.01) |

(52) U.S. Cl.
CPC ......... *C12N 9/1025* (2013.01); *C12N 9/0006* (2013.01); *C12N 9/0008* (2013.01); *C12N 9/88* (2013.01); *C12N 15/52* (2013.01); *C12P 5/02* (2013.01); *C12P 7/04* (2013.01); *C12P 7/24* (2013.01); *C12P 7/40* (2013.01); *C12P 7/44* (2013.01); *C12Y 101/01085* (2013.01); *C12Y 102/01048* (2013.01); *C12Y 203/03013* (2013.01); *C12Y 402/01033* (2013.01)

(58) Field of Classification Search
CPC .... C12N 9/1025; C12N 9/0008; C12N 15/52; C12N 9/0006; C12N 9/88; C12P 5/02; C12P 7/44; C12P 7/04; C12P 7/24; C12P 7/40; C12Y 102/01048; C12Y 101/01085; C12Y 203/03013; C12Y 402/01033
See application file for complete search history.

(56) References Cited

U.S. PATENT DOCUMENTS

| | | |
|---|---|---|
| 8,232,089 B2 | 7/2012 | Urano et al. |
| 8,298,798 B2 | 10/2012 | Liao et al. |
| 2011/0201083 A1 | 8/2011 | Liao et al. |
| 2012/0070868 A1 | 3/2012 | Lee et al. |
| 2014/0377857 A1 | 12/2014 | Liao et al. |
| 2015/0259710 A1 | 9/2015 | Dundon et al. |
| 2016/0355850 A1 | 12/2016 | Sanghani et al. |
| 2017/0232043 A1 | 8/2017 | Falb et al. |
| 2017/0369863 A1 | 12/2017 | Sanghani et al. |

FOREIGN PATENT DOCUMENTS

| | | | |
|---|---|---|---|
| WO | 2009046375 A2 | 4/2009 |
| WO | 2009096370 A1 | 8/2009 |
| WO | 2010045629 A2 | 4/2010 |
| WO | 2012135731 A2 | 10/2012 |

(Continued)

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Guo et al., PNAS 101(25):9205-9210, 2004.*
Office Action dated Jul. 16, 2020 pertaining to U.S. Appl. No. 16/338,098, filed Mar. 29, 2019, 19 pgs.

(Continued)

*Primary Examiner* — Delia M Ramirez
(74) *Attorney, Agent, or Firm* — Dinsmore & Shohl LLP

(57) ABSTRACT

Genetically modified LeuCD' enzyme complexes, processes for preparing a $C_7$-$C_{11}$ 2-ketoacid utilizing genetically modified LeuCD' enzyme complexes, and microbial organisms including modified LeuCD enzyme complexes are described. The instantly-disclosed genetically modified LeuCD' enzyme complexes, processes for preparing a $C_7$-$C_{11}$ 2-ketoacid, and microbial organisms including modified LeuCD' enzyme complexes can be particularly useful for producing $C_6$-$C_{10}$ aldehydes, alkanes, alcohols, and carboxylic acids, both in vivo and in vitro.

7 Claims, 9 Drawing Sheets
Specification includes a Sequence Listing.

(56) References Cited

FOREIGN PATENT DOCUMENTS

WO    2015089127 A1    6/2015

OTHER PUBLICATIONS

Devos et al., (Proteins: Structure, Function and Genetics, 2000, vol. 41: 98-107.
Whisstock et al., (Quarterly Reviews of Biophysics 2003, vol. 36 (3): 307-340.
Kisselev L., (Structure, 2002, vol. 10: 8-9.
Atsumi et al., "Non-Fermentative Pathways for Synthesis of Branched-Chain Higher Alcohols as Biofuels", Nature, 2008, vol. 451, 86-90, Nature Publishing Group.
Becker et al., "Bio-Based Production of Chemicals, Materials and Fuels—Corynebacterium Glutamicum as Versatile Cell Factory", Current Opinion in Biotechnology, 2012, 23, 631-640, Elsevier.
Becker et al., "Systems and Synthetic Metabolic Engineering for Amino Acid Production—The Heartbeat of Industrial Strain Development", Current Opinion in Biotechnology, 2012, 23, 718-726, Elsevier.
Choi et al., "Microbial Production of Short-Chain Alkanes", Nature, 2013, 502, 571-576, Macmillan Publishers.
Datsenko et al., "One-Step Inactivation of Chromosomal Genes in *Escherichia coli* K-12 Using PCR Products", Proc. Natl. Acad. Sci. USA, 2000, 97:12, 6640-6645.
Gronenberg et al., "Next Generation Biofuel Engineering in Prokaryotes", Current Opinion in Biotechnology, 2013, 17, 462-471, Elsevier.
Holton et al., "Structural Characterization of a D-Isomer Specific 2-Hydroxyacid Dehydrogenase from *Lactobacillus delbrueckii* ssp. Bulgaricus", Journal of Structural Biology, 2013, 181, 179-184, Elsevier Inc.
Hummel, Werner, "Large-Scale Applications of NAD(P)-Dependent Oxidoreductases: Recent Developments", Tibtech, 1999, 17, 487-492, Elsevier Science Ltd.
Koon et al., "Crystal Structure of LeuA from *Mycobacterium tuberculosis*, a Key Enzyme in Leucine Biosynthesis", Proc. Natl. Acad. Sci. USA, 2004, 101:22, 8295-8300.
Manikandan et al., "Structural Studies on the Enzyme Complex Isopropylmalate Isomerase [LeuCD] from *Mycobacterium tuberculosis*", Proteins, 2010, 35-49, Wiley-Liss, Inc.
Spaepen et al., "Characterization of Phenylpyruvate Decarboxylase, Involved in Auxin Production of Azospirillum Brasilense", Journal of Bacteriology, 2007, 189:21, 7626-7633.
Vedha-Peters et al., "Creation of a Broad-Range and Highly Stereoselective D-Amino Acid Dehydrogenase for the One-Step Synthesis of D-Amino Acids", J. Am. Chem. Soc., 2006, 128, 10923-10929, American Chemical Society.
Versees et al., "The Crystal Structure of Phenylpyruvate Decarboxylase from Azospirillum Brasilense at 1.5 A Resolution Implications for its Catalytic and Regulatory Mechanism", The FEBS Journal, 2007, 274, 2363-2375, The Authors Journal compilation.
Xiong et al., "A Bio-Catalytic Approach to Aliphatic Ketones", Scientific Reports, 2:311, doi: 10.1035/srep0311.
Zhang et al., "A Synthetic Metabolic Pathway for Production of the Platform Chemical Isobutyric Acid", ChemSusChem, 2011, 4, 1068-1070 Wiley-VCH Verlag GmbH & Co.
International Search Report and Written Opinion pertaining to PCT/US2015/064879 dated Mar. 22, 2016.
International Search Report and Written Opinion pertaining to PCT/US2016/069430 dated Jul. 4, 2017.
International Search Report and Written Opinion pertaining to PCT/US2016/069476 dated Jul. 4, 2017.
Felnagle et al., "Engineering Synthetic Recursive Pathways to Generate Non-Natural Small Molecules", Nature Chemical Biology, Jun. 2012, 518-526, vol. 8, Nature America, Inc.
Han et al., "Sites and Mechanisms of Aconitase Inactivation by Peroxynitrite: Modulation by Citrate and Glutathione", Biochemistry, 2005, 11986-11996, 44, American Chemical Society.
Hsu et al., "Leucine Biosynthesis in *Saccharomyces cerevisiae*, Purification and Characterization of b-Isopropylmalate Dehydrogenase", The Journal of Biological Chemistry, 1980, 7255-7260, vol. 255 No. 15.
Imada et al., "Structure of 3-Isopropylmalate Dehydrogenase in Complex with 3-Isopropylmalate at 2.0 A Resolution: the Role of Glu88 in the Unique Substrate-Recognition Mechanism", Structure, Aug. 1998, 971-982, 6, Current Biology Publications ISSN 0969-2126.
International Search Report and Written Opinion dated Mar. 18, 2015 pertaining to International Application No. PCT/US2014/069438.
Lee et al., "Metabolic Engineering of Clostridium Acetobutylicum M5 for Highly Selective Butanol Production", Biotechnology Journal, 2009, 1432-1440, 4, Wiley-VCH Verlag GmbH & Co.
Marcheschi et al., "A Synthetic Recursive '+1' Pathway for Carbon Chain Elongation", ACS Chemical Biology, 2012, 689-697, 7, American Chemical Society.
Sanghani et al., "Kinetic Mechanism of Human Glutathione-Dependent Formaldehyde Dehydrogenase", Biochemistry, 2000, 10720-10729, 39, American Chemical Society.
Shen et al., "A Synthetic Iterative Pathway for Ketoacid Elongation", Methods in Enzymology, 2011, 469-481, 497, Elsevier Inc.
Wang et al., "Optimization of Butanol Production from Tropical Maize Stalk Juice by Fermentation with Clostridium Beijerinckii NCIMB 8052", Bioresource Technology, 2011, 9985-9990, 102, Elsevier Ltd.
Zhang et al., "Expanding Metabolism for Biosynthesis of Non-natural Alcohols", PNAS, Dec. 2008, 20653-20658, vol. 105 No. 52, The National Academy of Science of the USA.
Rude et al., "New Microbial Fuels: A Biotech Perspective", Current Opinion in Microbiology, 2009, 274-281.
Zhang et al., "Subdomain II of alpha-isopropylmalate synthase is essential for activity: inferring a mechanism of feedback inhibition", The Journal of biological chemistry 2014, 289, 27966-27978.
Office Action pertaining to U.S. Appl. No. 15/030,616 dated Sep. 13, 2017.
Office Action pertianing to U.S. Appl. No. 15/533,390, dated Jun. 6, 2018.
Notice of Allowance and Fee(s) due dated Jan. 7, 2021 pertaining to U.S. Appl. No. 16/338,098, filed Mar. 29, 2019, 14 pgs.

* cited by examiner

FIG. 4

Ecoli-LeuC  MAKTLYEKLFDAHMVYEAENETPLLYIDRHLVHEVTSPQAFDGLRAHGRPVRQPG

Ecoli-LeuC  KTFATMDHNVSTQTKDINACGEMARIQMELIKNCKEEGVELYDLNHPYQGIVHV

Ecoli-LeuC  MGPEQGVTLPGMTIVCGDSHTATHGAFGALAFGIGTSEVEHVLATQTLKQGRAKT

Ecoli-LeuC  MKIEVQGKAAPGITAKDIVLAIGKTGSAGGTGHVVEFCGEAIRDLSMEGRMTLC

Ecoli-LeuC  NMAIEMGAKAGLVAPDETTENYVKGRLHAPKGKDFDDAVAYWKTLQTDEGATEDT

Ecoli-LeuC  VVTLQAEEISPQVTWGTNPGQVISVNDNIPDPASFADPVERASAEKALAYMGLKP

Ecoli-LeuC  GIPLTEVAIDKVFIGSCTNSRIEDLRAAAEIAKGRKVAPGVQAILVPGSGPVKAQ

Ecoli-LeuC  AEAEGLDKIFIEAGFEWRLPGCSMCLAMNDRLNPGERCASTSNRNFEGRQRGG

Ecoli-LeuC  RTHLVSPAMAAAAVTGHFADIRNIK

FIG. 5

Ecoli-LeuD  MAEKEIKHTGLVPLDAANVDTDAIPKQFLQKVTRTGFAAHLFNDVRFLDEKGQ

Ecoli-LeuD  QPNPDFVLNFPQYQGASILLARENFGGSSREHAPWALTDYGFKVVIAPSFADIF

Ecoli-LeuD  YGNSFNNQLLPVKLSDAEVDELFALVKANPGIHFDVDLEAQEVKAGEKTYRFTID

Ecoli-LeuD  AFRRHCMMNGLDSIGLTLQHDDAIAAYEAKQPAFMN

SEQUENCE LISTING

```
<160> NUMBER OF SEQ ID NOS: 37

<210> SEQ ID NO 1
<211> LENGTH: 466
<212> TYPE: PRT
<213> ORGANISM: Escherichia coli

<400> SEQUENCE: 1

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Val Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
```

```
                100                 105                 110
Pro Glu Gln Gly Val Thr Leu Pro Gly Met Thr Ile Val Cys Gly Asp
            115                 120                 125

Ser His Thr Ala Thr His Gly Ala Phe Gly Ala Leu Ala Phe Gly Ile
            130                 135             140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Leu Ala Met Asn Asn Asp
                405                 410                 415

Arg Leu Asn Pro Gly Glu Arg Cys Ala Ser Thr Ser Asn Arg Asn Phe
            420                 425                 430

Glu Gly Arg Gln Gly Arg Gly Gly Arg Thr His Leu Val Ser Pro Ala
        435                 440                 445

Met Ala Ala Ala Ala Val Thr Gly His Phe Ala Asp Ile Arg Asn
450                 455                 460

Ile Lys
465

<210> SEQ ID NO 2
<211> LENGTH: 201
<212> TYPE: PRT
<213> ORGANISM: Escherichia coli

<400> SEQUENCE: 2
```

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
                35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
            195                 200

<210> SEQ ID NO 3
<211> LENGTH: 466
<212> TYPE: PRT
<213> ORGANISM: Artificial Sequence
<220> FEATURE:
<223> OTHER INFORMATION: Synthesized - Modified LeuC (V35A)

<400> SEQUENCE: 3

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Ala Thr Ser Pro Gln Ala Phe Asp Gly Leu Arg Ala His Gly
            35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
                100                 105                 110

Pro Glu Gln Gly Val Thr Leu Pro Gly Met Thr Ile Val Cys Gly Asp
            115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

```
Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
    370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Leu Ala Met Asn Asn Asp
                405                 410                 415

Arg Leu Asn Pro Gly Glu Arg Cys Ala Ser Thr Ser Asn Arg Asn Phe
            420                 425                 430

Glu Gly Arg Gln Gly Arg Gly Arg Thr His Leu Val Ser Pro Ala
        435                 440                 445

Met Ala Ala Ala Ala Val Thr Gly His Phe Ala Asp Ile Arg Asn
    450                 455                 460

Ile Lys
465

<210> SEQ ID NO 4
<211> LENGTH: 466
<212> TYPE: PRT
<213> ORGANISM: Artificial Sequence
<220> FEATURE:
<223> OTHER INFORMATION: Synthesized - Modified LeuC (V35G)

<400> SEQUENCE: 4

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
                20                  25                  30

His Glu Gly Thr Ser Pro Gln Ala Phe Asp Gly Leu Arg Ala His Gly
            35                  40                  45
```

-continued

Arg Pro Val Arg Gln Pro Gly Lys Thr Phe Ala Thr Met Asp His Asn
 50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
    370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Leu Ala Met Asn Asn Asp
                405                 410                 415

Arg Leu Asn Pro Gly Glu Arg Cys Ala Ser Thr Ser Asn Arg Asn Phe
            420                 425                 430

Glu Gly Arg Gln Gly Arg Gly Arg Thr His Leu Val Ser Pro Ala
        435                 440                 445

Met Ala Ala Ala Ala Val Thr Gly His Phe Ala Asp Ile Arg Asn
450                 455                 460

Ile Lys

<210> SEQ ID NO 5
<211> LENGTH: 466
<212> TYPE: PRT
<213> ORGANISM: Artificial Sequence
<220> FEATURE:
<223> OTHER INFORMATION: Synthezied - Modified LeuC (L411A)

<400> SEQUENCE: 5

```
Met Ala Lys Thr Leu Tyr Glu Lys Leu Phe Asp Ala His Val Val Tyr
  1               5                  10                  15

Glu Ala Glu Asn Glu Thr Pro Leu Leu Tyr Ile Asp Arg His Leu Val
             20                  25                  30

His Glu Val Thr Ser Pro Gln Ala Phe Asp Gly Leu Arg Ala His Gly
         35                  40                  45

Arg Pro Val Arg Gln Pro Gly Lys Thr Phe Ala Thr Met Asp His Asn
     50                  55                  60

Val Ser Thr Gln Thr Lys Asp Ile Asn Ala Cys Gly Glu Met Ala Arg
 65                  70                  75                  80

Ile Gln Met Gln Glu Leu Ile Lys Asn Cys Lys Glu Phe Gly Val Glu
                 85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
```

```
                355                 360                 365
Pro Gly Val Gln Ala Leu Val Val Pro Gly Ser Gly Pro Val Lys Ala
    370                 375                 380
Gln Ala Glu Ala Glu Gly Leu Asp Lys Ile Phe Ile Glu Ala Gly Phe
385                 390                 395                 400
Glu Trp Arg Leu Pro Gly Cys Ser Met Cys Ala Ala Met Asn Asn Asp
                405                 410                 415
Arg Leu Asn Pro Gly Glu Arg Cys Ala Ser Thr Ser Asn Arg Asn Phe
            420                 425                 430
Glu Gly Arg Gln Gly Arg Gly Arg Thr His Leu Val Ser Pro Ala
        435                 440                 445
Met Ala Ala Ala Ala Val Thr Gly His Phe Ala Asp Ile Arg Asn
    450                 455                 460
Ile Lys
465

<210> SEQ ID NO 6
<211> LENGTH: 466
<212> TYPE: PRT
<213> ORGANISM: Artificial Sequence
<220> FEATURE:
<223> OTHER INFORMATION: Synthesized - Modified LeuC (L411G)

<400> SEQUENCE: 6

Met Ala Lys Thr Leu Tyr Glu Lys Leu Phe Asp Ala His Val Val Tyr
1               5                   10                  15
Glu Ala Glu Asn Glu Thr Pro Leu Leu Tyr Ile Asp Arg His Leu Val
            20                  25                  30
His Glu Val Thr Ser Pro Gln Ala Phe Asp Gly Leu Arg Ala His Gly
        35                  40                  45
Arg Pro Val Arg Gln Pro Gly Lys Thr Phe Ala Thr Met Asp His Asn
    50                  55                  60
Val Ser Thr Gln Thr Lys Asp Ile Asn Ala Cys Gly Glu Met Ala Arg
65                  70                  75                  80
Ile Gln Met Gln Glu Leu Ile Lys Asn Cys Lys Glu Phe Gly Val Glu
                85                  90                  95
Leu Tyr Asp Leu Asn His Pro Tyr Gln Gly Ile Val His Val Met Gly
            100                 105                 110
Pro Glu Gln Gly Val Thr Leu Pro Gly Met Thr Ile Val Cys Gly Asp
        115                 120                 125
Ser His Thr Ala Thr His Gly Ala Phe Gly Ala Leu Ala Phe Gly Ile
    130                 135                 140
Gly Thr Ser Glu Val Glu His Val Leu Ala Thr Gln Thr Leu Lys Gln
145                 150                 155                 160
Gly Arg Ala Lys Thr Met Lys Ile Glu Val Gln Gly Lys Ala Ala Pro
                165                 170                 175
Gly Ile Thr Ala Lys Asp Ile Val Leu Ala Ile Gly Lys Thr Gly
            180                 185                 190
Ser Ala Gly Gly Thr Gly His Val Val Glu Phe Cys Gly Glu Ala Ile
        195                 200                 205
Arg Asp Leu Ser Met Glu Gly Arg Met Thr Leu Cys Asn Met Ala Ile
    210                 215                 220
Glu Met Gly Ala Lys Ala Gly Leu Val Ala Pro Asp Glu Thr Thr Phe
225                 230                 235                 240
Asn Tyr Val Lys Gly Arg Leu His Ala Pro Lys Gly Lys Asp Phe Asp
```

```
                    245                 250                 255
Asp Ala Val Ala Tyr Trp Lys Thr Leu Gln Thr Asp Glu Gly Ala Thr
                260                 265                 270

Phe Asp Thr Val Val Thr Leu Gln Ala Glu Glu Ile Ser Pro Gln Val
            275                 280                 285

Thr Trp Gly Thr Asn Pro Gln Val Ile Ser Val Asn Asp Asn Ile
        290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
                355                 360                 365

Pro Gly Val Gln Ala Leu Val Val Pro Gly Ser Gly Pro Val Lys Ala
        370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Gly Ala Met Asn Asn Asp
                405                 410                 415

Arg Leu Asn Pro Gly Glu Arg Cys Ala Ser Thr Ser Asn Arg Asn Phe
            420                 425                 430

Glu Gly Arg Gln Gly Arg Gly Arg Thr His Leu Val Ser Pro Ala
                435                 440                 445

Met Ala Ala Ala Ala Val Thr Gly His Phe Ala Asp Ile Arg Asn
    450                 455                 460

Ile Lys
465

<210> SEQ ID NO 7
<211> LENGTH: 466
<212> TYPE: PRT
<213> ORGANISM: Artificial Sequence
<220> FEATURE:
<223> OTHER INFORMATION: Synthesized - Modified LeuC (L411V)

<400> SEQUENCE: 7

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Val Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
```

```
            130                 135                 140
Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
                180                 185                 190

Ser Ala Gly Gly Thr Gly His Val Val Glu Phe Cys Gly Glu Ala Ile
            195                 200                 205

Arg Asp Leu Ser Met Glu Gly Arg Met Thr Leu Cys Asn Met Ala Ile
        210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
    370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Val Ala Met Asn Asn Asp
                405                 410                 415

Arg Leu Asn Pro Gly Glu Arg Cys Ala Ser Thr Ser Asn Arg Asn Phe
            420                 425                 430

Glu Gly Arg Gln Gly Arg Gly Arg Thr His Leu Val Ser Pro Ala
        435                 440                 445

Met Ala Ala Ala Ala Val Thr Gly His Phe Ala Asp Ile Arg Asn
    450                 455                 460

Ile Lys
465

<210> SEQ ID NO 8
<211> LENGTH: 466
<212> TYPE: PRT
<213> ORGANISM: Artificial Sequence
<220> FEATURE:
<223> OTHER INFORMATION: Synthesized - Modified LeuC (V35A L411A)

<400> SEQUENCE: 8

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
```

```
                20                  25                  30
His Glu Ala Thr Ser Pro Gln Ala Phe Asp Gly Leu Arg Ala His Gly
                35                  40                  45

Arg Pro Val Arg Gln Pro Gly Lys Thr Phe Ala Thr Met Asp His Asn
 50                  55                  60

Val Ser Thr Gln Thr Lys Asp Ile Asn Ala Cys Gly Glu Met Ala Arg
 65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
                100                 105                 110

Pro Glu Gln Gly Val Thr Leu Pro Gly Met Thr Ile Val Cys Gly Asp
                115                 120                 125

Ser His Thr Ala Thr His Gly Ala Phe Gly Ala Leu Ala Phe Gly Ile
                130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
                180                 185                 190

Ser Ala Gly Gly Thr Gly His Val Val Glu Phe Cys Gly Glu Ala Ile
                195                 200                 205

Arg Asp Leu Ser Met Glu Gly Arg Met Thr Leu Cys Asn Met Ala Ile
                210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
                260                 265                 270

Phe Asp Thr Val Val Thr Leu Gln Ala Glu Glu Ile Ser Pro Gln Val
                275                 280                 285

Thr Trp Gly Thr Asn Pro Gly Gln Val Ile Ser Val Asn Asp Asn Ile
                290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
                340                 345                 350

Glu Asp Leu Arg Ala Ala Ala Glu Ile Ala Lys Gly Arg Lys Val Ala
                355                 360                 365

Pro Gly Val Gln Ala Leu Val Val Pro Gly Ser Gly Pro Val Lys Ala
                370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Ala Ala Met Asn Asn Asp
                405                 410                 415

Arg Leu Asn Pro Gly Glu Arg Cys Ala Ser Thr Ser Asn Arg Asn Phe
                420                 425                 430

Glu Gly Arg Gln Gly Arg Gly Gly Arg Thr His Leu Val Ser Pro Ala
                435                 440                 445
```

```
Met Ala Ala Ala Ala Val Thr Gly His Phe Ala Asp Ile Arg Asn
            450                 455                 460
Ile Lys
465

<210> SEQ ID NO 9
<211> LENGTH: 466
<212> TYPE: PRT
<213> ORGANISM: Artificial Sequence
<220> FEATURE:
<223> OTHER INFORMATION: Synthesized - Modified LeuC (V35A L411G)

<400> SEQUENCE: 9

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Ala Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335
```

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
    370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Gly Ala Met Asn Asn Asp
                405                 410                 415

Arg Leu Asn Pro Gly Glu Arg Cys Ala Ser Thr Ser Asn Arg Asn Phe
            420                 425                 430

Glu Gly Arg Gln Gly Arg Gly Gly Arg Thr His Leu Val Ser Pro Ala
        435                 440                 445

Met Ala Ala Ala Ala Val Thr Gly His Phe Ala Asp Ile Arg Asn
    450                 455                 460

Ile Lys
465

<210> SEQ ID NO 10
<211> LENGTH: 466
<212> TYPE: PRT
<213> ORGANISM: Artificial Sequence
<220> FEATURE:
<223> OTHER INFORMATION: Synthesized - Modified LeuC (V35A L411V)

<400> SEQUENCE: 10

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Ala Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
            245                 250                 255

Asp Ala Val Ala Tyr Trp Lys Thr Leu Gln Thr Asp Glu Gly Ala Thr
        260                 265                 270

Phe Asp Thr Val Val Thr Leu Gln Ala Glu Glu Ile Ser Pro Gln Val
    275                 280                 285

Thr Trp Gly Thr Asn Pro Gly Gln Val Ile Ser Val Asn Asp Asn Ile
290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
            325                 330                 335

Val Ala Ile Asp Lys Val Phe Ile Gly Ser Cys Thr Asn Ser Arg Ile
        340                 345                 350

Glu Asp Leu Arg Ala Ala Ala Glu Ile Ala Lys Gly Arg Lys Val Ala
    355                 360                 365

Pro Gly Val Gln Ala Leu Val Val Pro Gly Ser Gly Pro Val Lys Ala
370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Val Ala Met Asn Asn Asp
            405                 410                 415

Arg Leu Asn Pro Gly Glu Arg Cys Ala Ser Thr Ser Asn Arg Asn Phe
        420                 425                 430

Glu Gly Arg Gln Gly Arg Gly Arg Thr His Leu Val Ser Pro Ala
    435                 440                 445

Met Ala Ala Ala Ala Val Thr Gly His Phe Ala Asp Ile Arg Asn
    450                 455                 460

Ile Lys
465

<210> SEQ ID NO 11
<211> LENGTH: 466
<212> TYPE: PRT
<213> ORGANISM: Artificial Sequence
<220> FEATURE:
<223> OTHER INFORMATION: Synthesized - Modified LeuC (V35G L411A)

<400> SEQUENCE: 11

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Gly Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
    115                 120                 125

Ser His Thr Ala Thr His Gly Ala Phe Gly Ala Leu Ala Phe Gly Ile
130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
                180                 185                 190

Ser Ala Gly Gly Thr Gly His Val Val Glu Phe Cys Gly Glu Ala Ile
            195                 200                 205

Arg Asp Leu Ser Met Glu Gly Arg Met Thr Leu Cys Asn Met Ala Ile
            210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Glu Ile Ala Lys Gly Arg Lys Val Ala
            355                 360                 365

Pro Gly Val Gln Ala Leu Val Val Pro Gly Ser Gly Pro Val Lys Ala
    370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Ala Ala Met Asn Asn Asp
                405                 410                 415

Arg Leu Asn Pro Gly Glu Arg Cys Ala Ser Thr Ser Asn Arg Asn Phe
            420                 425                 430

Glu Gly Arg Gln Gly Arg Gly Gly Arg Thr His Leu Val Ser Pro Ala
            435                 440                 445

Met Ala Ala Ala Ala Val Thr Gly His Phe Ala Asp Ile Arg Asn
450                 455                 460

Ile Lys
465

<210> SEQ ID NO 12
<211> LENGTH: 466
<212> TYPE: PRT
<213> ORGANISM: Artificial Sequence
<220> FEATURE:
<223> OTHER INFORMATION: Synthesized - Modified LeuC (V35G L411G)

<400> SEQUENCE: 12

```
Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
                20                  25                  30

His Glu Gly Thr Ser Pro Gln Ala Phe Asp Gly Leu Arg Ala His Gly
            35                  40                  45

Arg Pro Val Arg Gln Pro Gly Lys Thr Phe Ala Thr Met Asp His Asn
        50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
                100                 105                 110

Pro Glu Gln Gly Val Thr Leu Pro Gly Met Thr Ile Val Cys Gly Asp
            115                 120                 125

Ser His Thr Ala Thr His Gly Ala Phe Gly Ala Leu Ala Phe Gly Ile
130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
            195                 200                 205

Arg Asp Leu Ser Met Glu Gly Arg Met Thr Leu Cys Asn Met Ala Ile
210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
    370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Gly Ala Met Asn Asn Asp
                405                 410                 415
```

```
Arg Leu Asn Pro Gly Glu Arg Cys Ala Ser Thr Ser Asn Arg Asn Phe
            420                 425                 430

Glu Gly Arg Gln Gly Arg Gly Gly Arg Thr His Leu Val Ser Pro Ala
            435                 440                 445

Met Ala Ala Ala Ala Val Thr Gly His Phe Ala Asp Ile Arg Asn
450                 455                 460

Ile Lys
465

<210> SEQ ID NO 13
<211> LENGTH: 466
<212> TYPE: PRT
<213> ORGANISM: Artificial Sequence
<220> FEATURE:
<223> OTHER INFORMATION: Synthesized - Modified LeuC (V35G L411V)

<400> SEQUENCE: 13

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Gly Thr Ser Pro Gln Ala Phe Asp Gly Leu Arg Ala His Gly
            35                  40                  45

Arg Pro Val Arg Gln Pro Gly Lys Thr Phe Ala Thr Met Asp His Asn
50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
            115                 120                 125

Ser His Thr Ala Thr His Gly Ala Phe Gly Ala Leu Ala Phe Gly Ile
130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
            195                 200                 205

Arg Asp Leu Ser Met Glu Gly Arg Met Thr Leu Cys Asn Met Ala Ile
210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
            275                 280                 285

Thr Trp Gly Thr Asn Pro Gly Gln Val Ile Ser Val Asn Asp Asn Ile
290                 295                 300
```

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
            325                 330                 335

Val Ala Ile Asp Lys Val Phe Ile Gly Ser Cys Thr Asn Ser Arg Ile
        340                 345                 350

Glu Asp Leu Arg Ala Ala Glu Ile Ala Lys Gly Arg Lys Val Ala
    355                 360                 365

Pro Gly Val Gln Ala Leu Val Val Pro Gly Ser Gly Pro Val Lys Ala
370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Val Ala Met Asn Asn Asp
                405                 410                 415

Arg Leu Asn Pro Gly Glu Arg Cys Ala Ser Thr Ser Asn Arg Asn Phe
                420                 425                 430

Glu Gly Arg Gln Gly Arg Gly Arg Thr His Leu Val Ser Pro Ala
                435                 440                 445

Met Ala Ala Ala Ala Val Thr Gly His Phe Ala Asp Ile Arg Asn
450                 455                 460

Ile Lys
465

<210> SEQ ID NO 14
<211> LENGTH: 201
<212> TYPE: PRT
<213> ORGANISM: Artificial Sequence
<220> FEATURE:
<223> OTHER INFORMATION: Synthesized - Modified LeuD (H88A)

<400> SEQUENCE: 14

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
                20                  25                  30

Lys Val Thr Arg Thr Gly Phe Gly Ala His Leu Phe Asn Asp Trp Arg
            35                  40                  45

Phe Leu Asp Glu Lys Gly Gln Gln Pro Asn Pro Asp Phe Val Leu Asn
        50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ala Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
        130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
            195                 200

<210> SEQ ID NO 15
<211> LENGTH: 201
<212> TYPE: PRT
<213> ORGANISM: Artificial Sequence
<220> FEATURE:
<223> OTHER INFORMATION: Synthesized - Modified LeuD (H88G)

<400> SEQUENCE: 15

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Gly Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
            195                 200

<210> SEQ ID NO 16
<211> LENGTH: 201
<212> TYPE: PRT
<213> ORGANISM: Artificial Sequence
<220> FEATURE:
<223> OTHER INFORMATION: Synthesized - Modified LeuD (H88V)

<400> SEQUENCE: 16

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Val Ala Pro Trp Ala Leu Thr Asp Tyr
                85                  90                  95

```
Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 17
<211> LENGTH: 201
<212> TYPE: PRT
<213> ORGANISM: Artificial Sequence
<220> FEATURE:
<223> OTHER INFORMATION: Synthesized - Modified LeuD (H88S)

<400> SEQUENCE: 17

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ser Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 18
<211> LENGTH: 201
<212> TYPE: PRT
<213> ORGANISM: Artificial Sequence
<220> FEATURE:
<223> OTHER INFORMATION: Synthesized - Modified LeuD (L31A)
```

-continued

```
<400> SEQUENCE: 18

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ala Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 19
<211> LENGTH: 201
<212> TYPE: PRT
<213> ORGANISM: Artificial Sequence
<220> FEATURE:
<223> OTHER INFORMATION: Synthesized - Modified LeuD (L31A H88A)

<400> SEQUENCE: 19

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ala Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ala Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
```

```
                    145                 150                 155                 160
Arg Phe Thr Ile Asp Ala Phe Arg Arg His Cys Met Met Asn Gly Leu
                    165                 170                 175

Asp Ser Ile Gly Leu Thr Leu Gln His Asp Asp Ala Ile Ala Ala Tyr
                    180                 185                 190

Glu Ala Lys Gln Pro Ala Phe Met Asn
                    195                 200

<210> SEQ ID NO 20
<211> LENGTH: 201
<212> TYPE: PRT
<213> ORGANISM: Artificial Sequence
<220> FEATURE:
<223> OTHER INFORMATION: Synthesized - Modified LeuD (L31A H88G)

<400> SEQUENCE: 20

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ala Gln
                    20                  25                  30

Lys Val Thr Arg Thr Gly Phe Gly Ala His Leu Phe Asn Asp Trp Arg
                    35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Gly Ala Pro Trp Ala Leu Thr Asp Tyr
                    85                  90                  95

Gly Phe Lys Val Val Ile Ala Pro Ser Phe Ala Asp Ile Phe Tyr Gly
                    100                 105                 110

Asn Ser Phe Asn Asn Gln Leu Leu Pro Val Lys Leu Ser Asp Ala Glu
                    115                 120                 125

Val Asp Glu Leu Phe Ala Leu Val Lys Ala Asn Pro Gly Ile His Phe
                    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                    165                 170                 175

Asp Ser Ile Gly Leu Thr Leu Gln His Asp Asp Ala Ile Ala Ala Tyr
                    180                 185                 190

Glu Ala Lys Gln Pro Ala Phe Met Asn
                    195                 200

<210> SEQ ID NO 21
<211> LENGTH: 201
<212> TYPE: PRT
<213> ORGANISM: Artificial Sequence
<220> FEATURE:
<223> OTHER INFORMATION: Synthesized - Modified LeuD (L31A H88V)

<400> SEQUENCE: 21

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ala Gln
                    20                  25                  30

Lys Val Thr Arg Thr Gly Phe Gly Ala His Leu Phe Asn Asp Trp Arg
                    35                  40                  45
```

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Val Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
                115                 120                 125

Val Asp Glu Leu Phe Ala Leu Val Lys Ala Asn Pro Gly Ile His Phe
130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
                180                 185                 190

Glu Ala Lys Gln Pro Ala Phe Met Asn
        195                 200

<210> SEQ ID NO 22
<211> LENGTH: 201
<212> TYPE: PRT
<213> ORGANISM: Artificial Sequence
<220> FEATURE:
<223> OTHER INFORMATION: Synthesized - Modified LeuD (L31A H88S)

<400> SEQUENCE: 22

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ala Gln
                20                  25                  30

Lys Val Thr Arg Thr Gly Phe Gly Ala His Leu Phe Asn Asp Trp Arg
            35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ser Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
                115                 120                 125

Val Asp Glu Leu Phe Ala Leu Val Lys Ala Asn Pro Gly Ile His Phe
130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
                180                 185                 190

Glu Ala Lys Gln Pro Ala Phe Met Asn
        195                 200

<210> SEQ ID NO 23
<211> LENGTH: 201
<212> TYPE: PRT
<213> ORGANISM: Artificial Sequence
<220> FEATURE:
<223> OTHER INFORMATION: Synthesized - Modified LeuD (L31G)

<400> SEQUENCE: 23

```
Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Gly Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200
```

<210> SEQ ID NO 24
<211> LENGTH: 201
<212> TYPE: PRT
<213> ORGANISM: Artificial Sequence
<220> FEATURE:
<223> OTHER INFORMATION: Synthesized - Modified LeuD (L31G H88A)

<400> SEQUENCE: 24

```
Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Gly Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ala Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110
```

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
                180                 185                 190

Glu Ala Lys Gln Pro Ala Phe Met Asn
            195                 200

<210> SEQ ID NO 25
<211> LENGTH: 201
<212> TYPE: PRT
<213> ORGANISM: Artificial Sequence
<220> FEATURE:
<223> OTHER INFORMATION: Synthesized - Modified LeuD (L31G H88G)

<400> SEQUENCE: 25

Met Ala Glu Lys Phe Ile Lys His Thr Gly Leu Val Val Pro Leu Asp
1               5                   10                  15

Ala Ala Asn Val Asp Thr Asp Ile Ile Pro Lys Gln Phe Gly Gln
            20                  25                  30

Lys Val Thr Arg Thr Gly Phe Gly Ala His Leu Phe Asn Asp Trp Arg
            35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Gly Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
                180                 185                 190

Glu Ala Lys Gln Pro Ala Phe Met Asn
            195                 200

<210> SEQ ID NO 26
<211> LENGTH: 201
<212> TYPE: PRT
<213> ORGANISM: Artificial Sequence
<220> FEATURE:
<223> OTHER INFORMATION: Synthesized - Modified LeuD (L31G H88V)

<400> SEQUENCE: 26

Met Ala Glu Lys Phe Ile Lys His Thr Gly Leu Val Val Pro Leu Asp

```
                1               5                      10                     15
            Ala Ala Asn Val Asp Thr Asp Ala Ile Ile Pro Lys Gln Phe Gly Gln
                            20                  25                  30

Lys Val Thr Arg Thr Gly Phe Gly Ala His Leu Phe Asn Asp Trp Arg
                            35                  40                  45

Phe Leu Asp Glu Lys Gly Gln Gln Pro Asn Pro Asp Phe Val Leu Asn
                50                      55                  60

Phe Pro Gln Tyr Gln Gly Ala Ser Ile Leu Leu Ala Arg Glu Asn Phe
            65                      70                  75                  80

Gly Cys Gly Ser Ser Arg Glu Val Ala Pro Trp Ala Leu Thr Asp Tyr
                            85                  90                  95

Gly Phe Lys Val Val Ile Ala Pro Ser Phe Ala Asp Ile Phe Tyr Gly
                            100                 105                 110

Asn Ser Phe Asn Asn Gln Leu Leu Pro Val Lys Leu Ser Asp Ala Glu
                            115                 120                 125

Val Asp Glu Leu Phe Ala Leu Val Lys Ala Asn Pro Gly Ile His Phe
                        130                 135                 140

Asp Val Asp Leu Glu Ala Gln Glu Val Lys Ala Gly Glu Lys Thr Tyr
            145                 150                 155                 160

Arg Phe Thr Ile Asp Ala Phe Arg Arg His Cys Met Met Asn Gly Leu
                                165                 170                 175

Asp Ser Ile Gly Leu Thr Leu Gln His Asp Asp Ala Ile Ala Ala Tyr
                            180                 185                 190

Glu Ala Lys Gln Pro Ala Phe Met Asn
                            195                 200

<210> SEQ ID NO 27
<211> LENGTH: 201
<212> TYPE: PRT
<213> ORGANISM: Artificial Sequence
<220> FEATURE:
<223> OTHER INFORMATION: Synthesized - Modified LeuD( L31G H88S)

<400> SEQUENCE: 27

Met Ala Glu Lys Phe Ile Lys His Thr Gly Leu Val Val Pro Leu Asp
            1               5                      10                     15

Ala Ala Asn Val Asp Thr Asp Ala Ile Ile Pro Lys Gln Phe Gly Gln
                            20                  25                  30

Lys Val Thr Arg Thr Gly Phe Gly Ala His Leu Phe Asn Asp Trp Arg
                            35                  40                  45

Phe Leu Asp Glu Lys Gly Gln Gln Pro Asn Pro Asp Phe Val Leu Asn
                50                      55                  60

Phe Pro Gln Tyr Gln Gly Ala Ser Ile Leu Leu Ala Arg Glu Asn Phe
            65                      70                  75                  80

Gly Cys Gly Ser Ser Arg Glu Ser Ala Pro Trp Ala Leu Thr Asp Tyr
                            85                  90                  95

Gly Phe Lys Val Val Ile Ala Pro Ser Phe Ala Asp Ile Phe Tyr Gly
                            100                 105                 110

Asn Ser Phe Asn Asn Gln Leu Leu Pro Val Lys Leu Ser Asp Ala Glu
                            115                 120                 125

Val Asp Glu Leu Phe Ala Leu Val Lys Ala Asn Pro Gly Ile His Phe
                        130                 135                 140

Asp Val Asp Leu Glu Ala Gln Glu Val Lys Ala Gly Glu Lys Thr Tyr
            145                 150                 155                 160

Arg Phe Thr Ile Asp Ala Phe Arg Arg His Cys Met Met Asn Gly Leu
```

```
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 28
<211> LENGTH: 201
<212> TYPE: PRT
<213> ORGANISM: Artificial Sequence
<220> FEATURE:
<223> OTHER INFORMATION: Synthesized - Modified LeuD (L31V)

<400> SEQUENCE: 28

Met Ala Glu Lys Phe Ile Lys His Thr Gly Leu Val Val Pro Leu Asp
1               5                  10                  15

Ala Ala Asn Val Asp Thr Asp Ala Ile Ile Pro Lys Gln Phe Val Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 29
<211> LENGTH: 201
<212> TYPE: PRT
<213> ORGANISM: Artificial Sequence
<220> FEATURE:
<223> OTHER INFORMATION: Synthesized - Modified LeuD (L31V H88A)

<400> SEQUENCE: 29

Met Ala Glu Lys Phe Ile Lys His Thr Gly Leu Val Val Pro Leu Asp
1               5                  10                  15

Ala Ala Asn Val Asp Thr Asp Ala Ile Ile Pro Lys Gln Phe Val Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
50                  55                  60
```

Phe Pro Gln Tyr Gln Gly Ala Ser Ile Leu Leu Ala Arg Glu Asn Phe
65                  70                  75                  80

Gly Cys Gly Ser Ser Arg Glu Ala Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
        130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 30
<211> LENGTH: 201
<212> TYPE: PRT
<213> ORGANISM: Artificial Sequence
<220> FEATURE:
<223> OTHER INFORMATION: Synthesized - Modified LeuD (L31V H88G)

<400> SEQUENCE: 30

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Val Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Gly Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
        130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 31
<211> LENGTH: 201

```
<212> TYPE: PRT
<213> ORGANISM: Artificial Sequence
<220> FEATURE:
<223> OTHER INFORMATION: Synthesized - Modified LeuD (L31V H88V)

<400> SEQUENCE: 31

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Val Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Val Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 32
<211> LENGTH: 201
<212> TYPE: PRT
<213> ORGANISM: Artificial Sequence
<220> FEATURE:
<223> OTHER INFORMATION: Synthesized - Modified LeuD (L31V H88S)

<400> SEQUENCE: 32

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Val Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ser Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125
```

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 33
<211> LENGTH: 201
<212> TYPE: PRT
<213> ORGANISM: Artificial Sequence
<220> FEATURE:
<223> OTHER INFORMATION: Synthesized - Modified LeuD (L31S)

<400> SEQUENCE: 33

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ser Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 34
<211> LENGTH: 201
<212> TYPE: PRT
<213> ORGANISM: Artificial Sequence
<220> FEATURE:
<223> OTHER INFORMATION: Synthesized - Modified LeuD (L31S H88A)

<400> SEQUENCE: 34

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ser Gln

```
            20                  25                  30
Lys Val Thr Arg Thr Gly Phe Gly Ala His Leu Phe Asn Asp Trp Arg
                35                  40                  45

Phe Leu Asp Glu Lys Gly Gln Gln Pro Asn Pro Asp Phe Val Leu Asn
         50                  55                  60

Phe Pro Gln Tyr Gln Gly Ala Ser Ile Leu Leu Ala Arg Glu Asn Phe
 65                  70                  75                  80

Gly Cys Gly Ser Ser Arg Glu Ala Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
                115                 120                 125

Val Asp Glu Leu Phe Ala Leu Val Lys Ala Asn Pro Gly Ile His Phe
            130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
                180                 185                 190

Glu Ala Lys Gln Pro Ala Phe Met Asn
            195                 200

<210> SEQ ID NO 35
<211> LENGTH: 201
<212> TYPE: PRT
<213> ORGANISM: Artificial Sequence
<220> FEATURE:
<223> OTHER INFORMATION: Synthesized - Modified LeuD (L31S H88G)

<400> SEQUENCE: 35

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ser Gln
                20                  25                  30

Lys Val Thr Arg Thr Gly Phe Gly Ala His Leu Phe Asn Asp Trp Arg
                35                  40                  45

Phe Leu Asp Glu Lys Gly Gln Gln Pro Asn Pro Asp Phe Val Leu Asn
         50                  55                  60

Phe Pro Gln Tyr Gln Gly Ala Ser Ile Leu Leu Ala Arg Glu Asn Phe
 65                  70                  75                  80

Gly Cys Gly Ser Ser Arg Glu Gly Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
                115                 120                 125

Val Asp Glu Leu Phe Ala Leu Val Lys Ala Asn Pro Gly Ile His Phe
            130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
```

Glu Ala Lys Gln Pro Ala Phe Met Asn
             195                 200

<210> SEQ ID NO 36
<211> LENGTH: 201
<212> TYPE: PRT
<213> ORGANISM: Artificial Sequence
<220> FEATURE:
<223> OTHER INFORMATION: Synthesized - Modified LeuD (L31S H88V)

<400> SEQUENCE: 36

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ser Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Val Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 37
<211> LENGTH: 201
<212> TYPE: PRT
<213> ORGANISM: Artificial Sequence
<220> FEATURE:
<223> OTHER INFORMATION: Synthesized - Modified LeuD (L31S H88S)

<400> SEQUENCE: 37

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ser Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

-continued

```
Gly Cys Gly Ser Ser Arg Glu Ser Ala Pro Trp Ala Leu Thr Asp Tyr
             85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
130                         135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
            195                 200
```

PROCESS TO PREPARE ELONGATED 2-KETOACIDS AND C-5-C10 COMPOUNDS THEREFROM VIA GENETIC MODIFICATIONS TO MICROBIAL METABOLIC PATHWAYS

CROSS-REFERENCE TO RELATED APPLICATIONS

This application claims the benefit of U.S. Provisional Application Ser. No. 62/402,586, filed Sep. 30, 2016, and also U.S. Provisional Application Ser. No. 62/402,569 filed Sep. 30, 2016, both of which are hereby incorporated by reference in their entirety.

SEQUENCE LISTING

This application incorporates by reference the material in the ASCII text file "79046-WO-PCT_SequenceListing.txt" of 94,000 bytes created on Aug. 23, 2016 and filed in U.S. Provisional Application Ser. No. 62/402,569, on Sep. 30, 2016.

FIELD

The present disclosure generally relates to genetically modified LeuCD' enzyme complexes, processes for preparing a $C_7$-$C_{11}$ 2-ketoacid utilizing genetically modified LeuCD' enzyme complexes, and microbial organisms including genetically modified LeuCD' enzyme complexes.

BACKGROUND

Concerns about the future scarcity, cost, and environmental impact of obtaining and using fossil fuels have stimulated interest in the exploitation of cheap, renewable biomass as an alternative source for both fuels and chemicals made therefrom. As crude oil prices have risen, bio-based chemicals and industrial products have become attractive alternatives to their petroleum-derived counterparts. Fermentation processes using anaerobic microbial organisms offer a promising path for converting biomass and agricultural waste into useful products, while at the same time remediating problems that may be encountered in disposal of low-value agricultural commodities and food processing byproducts/wastes. Some useful products that can be prepared from low-cost biomass feedstocks are $C_6$-$C_{10}$ aldehydes, $C_6$-$C_{10}$ alcohols, $C_6$-$C_{10}$ carboxylic acids, and $C_5$-$C_9$ alkanes, including, in particular, $C_6$-$C_{10}$ alcohols.

$C_6$-$C_{10}$ alcohols are produced using petrochemical and natural raw material processes. The petrochemical processes are based upon ethylene oligomerization. For example, the Ziegler process uses aluminum to mediate ethylene oligomerization at high pressure to generate tri-alkyl aluminum species. The tri-alkyl aluminum species are oxidized under dry air and hydrolyzed to yield a Poisson distribution of terminal alcohols ranging in length from $C_2$-$C_{26}$ (including an even number carbon chain atoms only). Hydroformylation of olefins produced by ethylene oligomerization such as, e.g., via the Shell higher olefin process (i.e., SHOP), followed by reduction produces alcohols having an odd number of carbon chain atoms. Conversion of fatty acids of natural oils such as, e.g., palm kernel and coconut, through oleochemical transformation of hydrogenation, transesterification, and reduction is also employed to produce long chain alcohols with the bulk of the alcohols having carbon chain lengths of greater than $C_{10}$. The lack of selectivity to narrow carbon chain length distribution is a significant drawback of current production methods. Further, the Ziegler process is also imperfect in that a co-product thereof is hydrated alumina (i.e., $Al_2O_3^-[H_2O]_x$). Thus, identification of better and less expensive methods to produce $C_6$-$C_{10}$ alcohols, $C_5$-$C_9$ alkanes, and $C_6$-$C_{10}$ carboxylic acids is desired. However, microbial organisms often fail to produce many of the petrochemical based products at economically viable rates or yields. For example, while metabolic engineering has been extensively employed to build pathways and/or channel metabolites toward a pathway of interest, ethanol is currently the most common biochemical produced using microbial organisms. Economically viable methods for producing $C_6$-$C_{10}$ alcohols and $C_6$-$C_{10}$ carboxylic acids are being actively pursued in both the biofuel and chemical industries.

Success in production of natural amino acids by microbial fermentation has generated significant interest in utilizing amino acid biosynthetic pathways for producing chemicals of interest, including longer chain alcohols, alkanes, and carboxylic acids. Of particular interest are 2-ketoacids, which are key intermediates in amino acid biosynthesis that can be exploited in the biosynthesis of chemicals inside cells. Three enzymes within the leucine biosynthetic pathway are involved in elongating 2-ketoacids and can operate to convert 2-ketobutyrate, 2-ketoisovalerate, and/or 2-methyl-2-ketopentanoate to a longer chain 2-ketoacids. These enzymes are generally referred to, without reference to any specific microbial organism, as isopropylmalate synthase, isopropylmalate isomerase, and isopropylmalate dehydrogenase. In E. coli specifically, these enzymes are referred to as LeuA (GenBank:Accession No. NC 000913.3 Gene ID: 947465). LeuB (GenBank:Accession NO. NC 000913.3 Gene ID: 944798), and LeuCD (GenBank:Accession No. NC 000913.3 Gene ID: 945076 and Gene ID: 945642), respectively. The feasibility of extending the length of 2-ketoacids inside cells via engineering of the LeuA gene product of E. coli has expanded the range of biochemicals that can be produced from 2-ketoacids. In E. coli, the products of LeuABCD genes extend the length of 2-ketoacids by one carbon unit. Such extension is observed during leucine biosynthesis, in which the products of LeuABCD genes work together to convert 2-ketoisovalerate (a 5-carbon acid) to 2-ketoisocaproate (a 6-carbon acid). Additionally, expansion of the active site of LeuA allowed for the recursive extension of the $C_4$ ketoacid, 2-ketobutyric acid (i.e., 2-ketobutyrate), to a $C_9$ 2-ketoacid, 2-ketononanoic acid (i.e., 2-keto-nonanoate). However, continued development and engineering of LeuABCD genes is needed to allow for efficient production of $C_7$-$C_{11}$ 2-ketoacids and to avoid major bottlenecks in the later stages of the pathway used to elongate the 2-ketoacids.

Accordingly, there exist ongoing needs for economically viable and efficient methods for producing longer chain aldehydes, alkanes, alcohols, and carboxylic acids.

SUMMARY

Embodiments of the present disclosure meet those needs by providing genetically modified LeuCD' enzyme complexes, processes for preparing a $C_7$-$C_{11}$ 2-ketoacid utilizing genetically modified LeuCD' enzyme complexes, and microbial organisms including genetically modified LeuCD' enzyme complexes. The genetically modified LeuCD' enzyme complexes, processes for preparing a $C_7$-$C_{11}$ 2-ketoacid, and microbial organisms including genetically modified LeuCD' enzyme complexes can be used to produce bio-based chemicals and industrial products as alternatives to fossil fuels. The instantly-disclosed genetically modified LeuCD' enzyme complexes, processes for preparing a $C_7$-$C_{11}$ 2-ketoacid, and microbial organisms including genetically modified LeuCD' enzyme complexes can be useful for producing longer chain aldehydes, alkanes, alcohols, and carboxylic acids, both in vivo and in vitro.

According to embodiments of the present disclosure, a LeuCD' enzyme complex is provided. The LeuCD' enzyme complex includes: (a) a LeuC subunit and (b) a LeuD subunit. The LeuC subunit (a) is selected from the group consisting of: (1) a native LeuC subunit including an amino acid sequence with at least 80% homology to SEQ ID NO: 1; and (2) a genetically modified LeuC subunit including an amino acid sequence with at least 80% homology to SEQ ID NO: 1 and at least one modification wherein alanine, glycine, or valine is independently substituted for Val-35. Leu-411, or a combination thereof. The LeuD subunit (b) is selected from the group consisting of: (1) a native LeuD subunit including an amino acid sequence with at least 80% homology to SEQ ID NO: 2; and (2) a genetically modified LeuD subunit including an amino acid sequence with at least 80% homology to SEQ ID NO: 2 and at least one modification wherein alanine, glycine, valine, or serine is independently substituted for Leu-31. His-88, or a combination thereof. The LeuCD' enzyme complex includes a combination of (a)(1) and (b)(2), a combination of (a)(2) and (b)(2), or a combination of (a)(2) and (b)(1), and the genetically modified LeuCD' enzyme complex has isopropylmalate isomerase activity.

According to other embodiments of the present disclosure, a process for preparing a $C_7$-$C_{11}$ 2-ketoacid is provided. The process includes providing at least one of a $C_4$-$C_{10}$ 2-ketoacid substrate with (A) at least one isopropylmalate synthase enzyme having isopropylmalate synthase activity, (B) at least one isopropylmalate dehydrogenase enzyme having isopropylmalate dehydrogenase activity, and (C) at least one genetically modified LeuCD' enzyme complex, under conditions that the at least one of the $C_4$-$C_{10}$ 2-ketoacid substrate is converted to the $C_7$-$C_{11}$ 2-ketoacid. The genetically modified LeuCD' enzyme complex includes (1) a LeuC subunit and (2) a LeuD subunit. The LeuC subunit (1) is selected from the group consisting of: (i) a native LeuC subunit including an amino acid sequence with at least 80% homology to SEQ ID NO: 1; and (ii) a genetically modified LeuC' subunit including an amino acid sequence with at least 80% homology to SEQ ID NO: 1 and at least one modification wherein alanine, glycine, or valine is independently substituted for Val-35. Lu-411, or a combination thereof. The LeuD subunit (2) is selected from the group consisting of: (i) a native LeuD subunit including an amino acid sequence with at least 80% homology to SEQ ID NO: 2; and (ii) a genetically modified LeuD' subunit including an amino acid sequence with at least 80% homology to SEQ ID NO: 2 and at least one modification wherein alanine, glycine, valine, or serine is independently substituted for Leu-31, His-88, or a combination thereof. The genetically modified LeuCD' enzyme complex includes a combination of (I)(C)(1)(i) and (1)(C)(2)(ii), a combination of (1)(C)(1)(ii) and (1)(C)(2)(ii), or a combination of (1)(C) (1)(ii) and (1)(C)(2)(i), and the genetically modified LeuCD' enzyme complex has isopropylmalate isomerase activity. The conversion of the at least one of the $C_4$-$C_{10}$ 2-ketoacid substrate to the $C_7$-$C_{11}$ 2-ketoacid occurs via one or more biochemical reactions.

In yet other embodiments of the present disclosure, a microbial organism including a genetically modified LeuCD' enzyme complex is provided. The genetically modified LeuCD' enzyme complex includes: (a) a LeuC subunit and (b) a LeuD subunit. The LeuC subunit (a) is selected from the group consisting of: (1) a native LeuC subunit including an amino acid sequence with at least 80% homology to SEQ ID NO: 1; and (2) a genetically modified LeuC subunit including an amino acid sequence with at least 80% homology to SEQ ID NO: 1 and at least one modification wherein alanine, glycine, or valine is independently substituted for Val-35, Leu-411, or a combination thereof. The LeuD subunit (b) is selected from: (1) a native LeuD subunit including an amino acid sequence with at least 80% homology to SEQ ID NO: 2; and (2) a genetically modified LeuD subunit including an amino acid sequence with at least 80% homology to SEQ ID NO: 2 and at least one modification wherein alanine, glycine, valine, or serine is independently substituted for Leu-31. His-88, or a combination thereof. The LeuCD' enzyme complex includes a combination of (a)(1) and (b)(2), a combination of (a)(2) and (b)(2), or a combination of (a)(2) and (b)(1), and the genetically modified LeuCD' enzyme complex has isopropylmalate isomerase activity.

It is understood that both the following summary and the detailed description are exemplary and explanatory and are intended to provide further explanation of the disclosure as claimed. Neither the summary nor the description that follows is intended to define or limit the scope of the disclosure to the particular features mentioned in the summary or description.

BRIEF DESCRIPTION OF THE DRAWINGS

FIG. 1 shows the elongation of a 2-ketoacid by the recursive activities of LeuABCD (termed "the LeuABCD pathway" in E. coli), as depicted in 1 to 3. Following the elongation, the resulting elongated 2-ketoacid (IV) is converted to an aldehyde (V), via the activity of a (thiamin dependent) decarboxylase in 4, and finally to an alcohol (VI) in 5, via the activity of an alcohol dehydrogenase.

FIG. 2 shows two related but different routes to produce 1-heptanol. In the first route, a Wood-Ljungdahl pathway converts synthesis gas to acetyl CoA, and another pathway then converts the acetyl CoA to pyruvate. The pyruvate is then converted to 2-ketobutyrate, and finally a LeuABCD pathway is initiated, wherein the 2-ketobutyrate is converted to $C_7$-$C_{11}$ 2-ketoacid (in this embodiment; 2-ketooctanoate). Once the elongated 2-ketoacid has been formed (the 2-ketooctanoate), a (thiamin dependent) decarboxylase converts it to a $C_6$-$C_{10}$ aldehyde (in this embodiment, heptanol), and an alcohol dehydrogenase converts it the $C_6$-$C_{10}$ aldehyde to a $C_6$-$C_{10}$ alcohol (in this embodiment, 1-heptanol). In the second route, one of the potential sugar catabolism pathways, which in this embodiment is a glycolysis or pentose phosphate pathway, converts a $C_5$ or $C_6$ sugar to pyruvate, and thereafter the same pathway sequence is followed as in the first route to reach the heptanol.

FIG. 3 shows a model of the LeuCD active site, which is formed at the interface of the LeuC subunit and the LeuD subunit. The model was created using homology modeling and using the crystal structures of pig aconitase (PDB ID code 1ACO) and isopropylmalate isomerase small subunit of Campylobacter jejuni (PDB ID code 3Q3W) as templates. The active site is modeled with the 2-hexylmalate (i.e., 2-H1M) and the 4Fe-4S cluster. Various combinations of the residues Val35 and Leu-411 in the LeuC subunit, and Leu-31 and His-88 in the LeuD subunit were modified in the instantly disclosed genetically modified LeuCD' enzyme complexes.

FIG. 4. Highly conserved amino acid residues in the large subunit of isopropylmalate isomerase. Shown are the highly conserved amino acid residues identified following an alignment of non-redundant protein sequences of the large subunit of isopropylmalate isomerase that diverged from the *E. coli* LeuC sequence by as much as 1-60%. Amino acid residues that were highly conserved across the protein sequences are shaded and are believed to play an important role in the functioning of the LeuC during the elongation of 2-ketoacids. Amino acid residues that are boxed are believed to form the active site of isopropylmalate isomerase.

FIG. 5. Highly conserved amino add residues in the small subunit of isopropylmalate isomerase. Shown are the highly conserved amino acid residues identified following an alignment of non-redundant protein sequences of the small subunit of isopropylmalate isomerase that diverged from the *E. coli* LeuD sequence by as much as 1-60%. Amino acid residues that were highly conserved across the protein sequences are shaded and are believed to play an important role in the functioning of the LeuD during the elongation of 2-ketoacids. Amino acid residues that are boxed are believed to form the active site of isopropylmalate isomerase.

Figure 6:
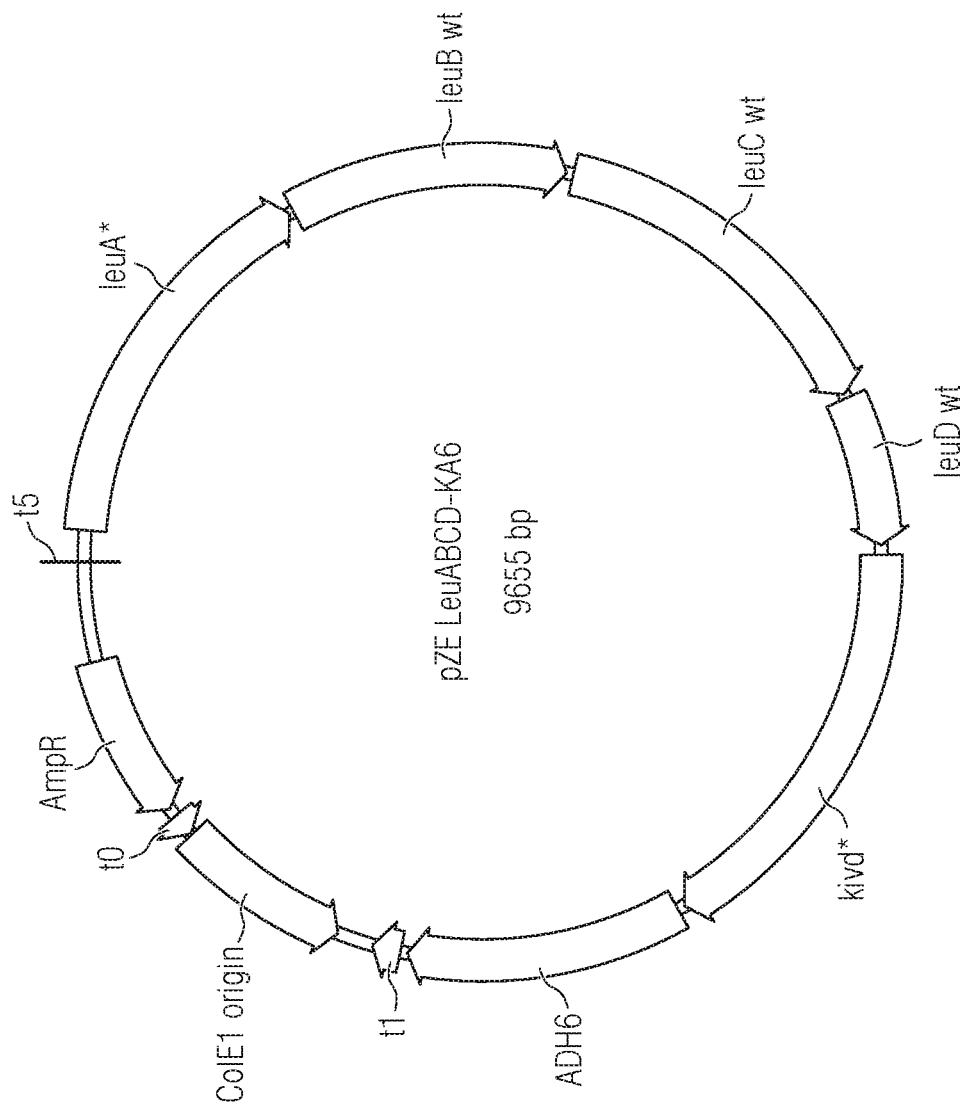

FIG. 6. The pZE_LeuABCD-KA6 vector. Shown is the pZE_LeuABCD-KA6 vector that was used with a modified vector, pOC-CL-###, for the alcohol production studies.

Figure 7:
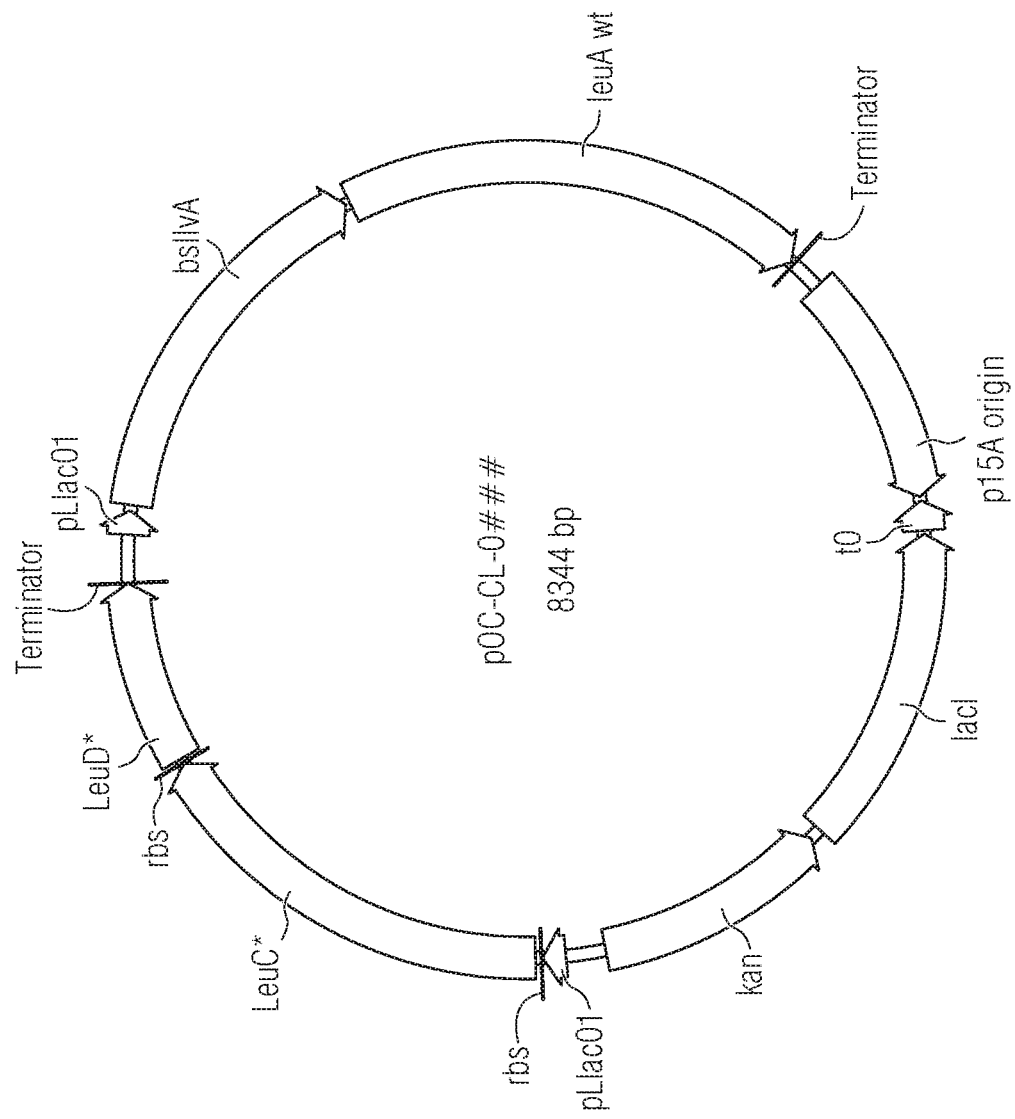

FIG. 7. The pOC-CL-0 ###vector. Shown is a typical modified pOC-CL-###vector that was used with the pZE_LeuABCD-KA6 vector for the alcohol production studies.

Figure 8A:
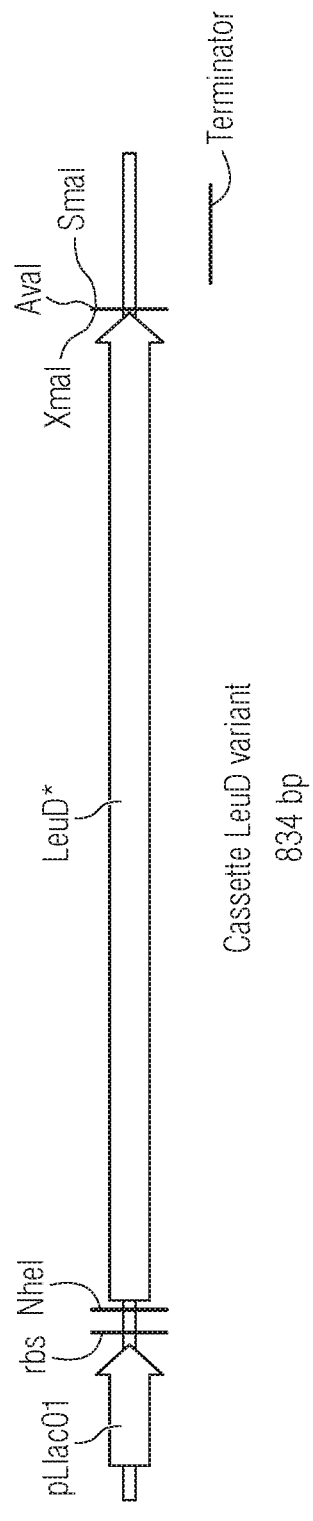
Figure 8B:
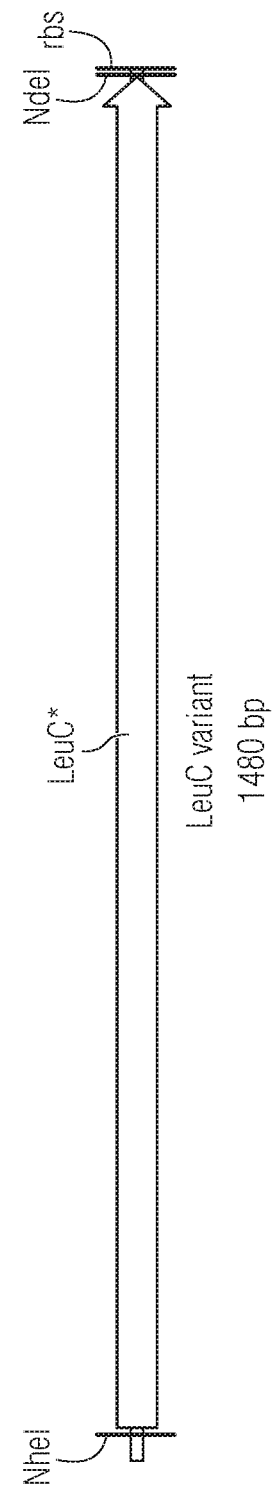

FIG. 8. Cassettes for LeuD and LeuC variants. FIG. 8A shows the LeuD variant gene cassette, while FIG. 8B shows the LeuC variant gene cassette.

Figure 9:
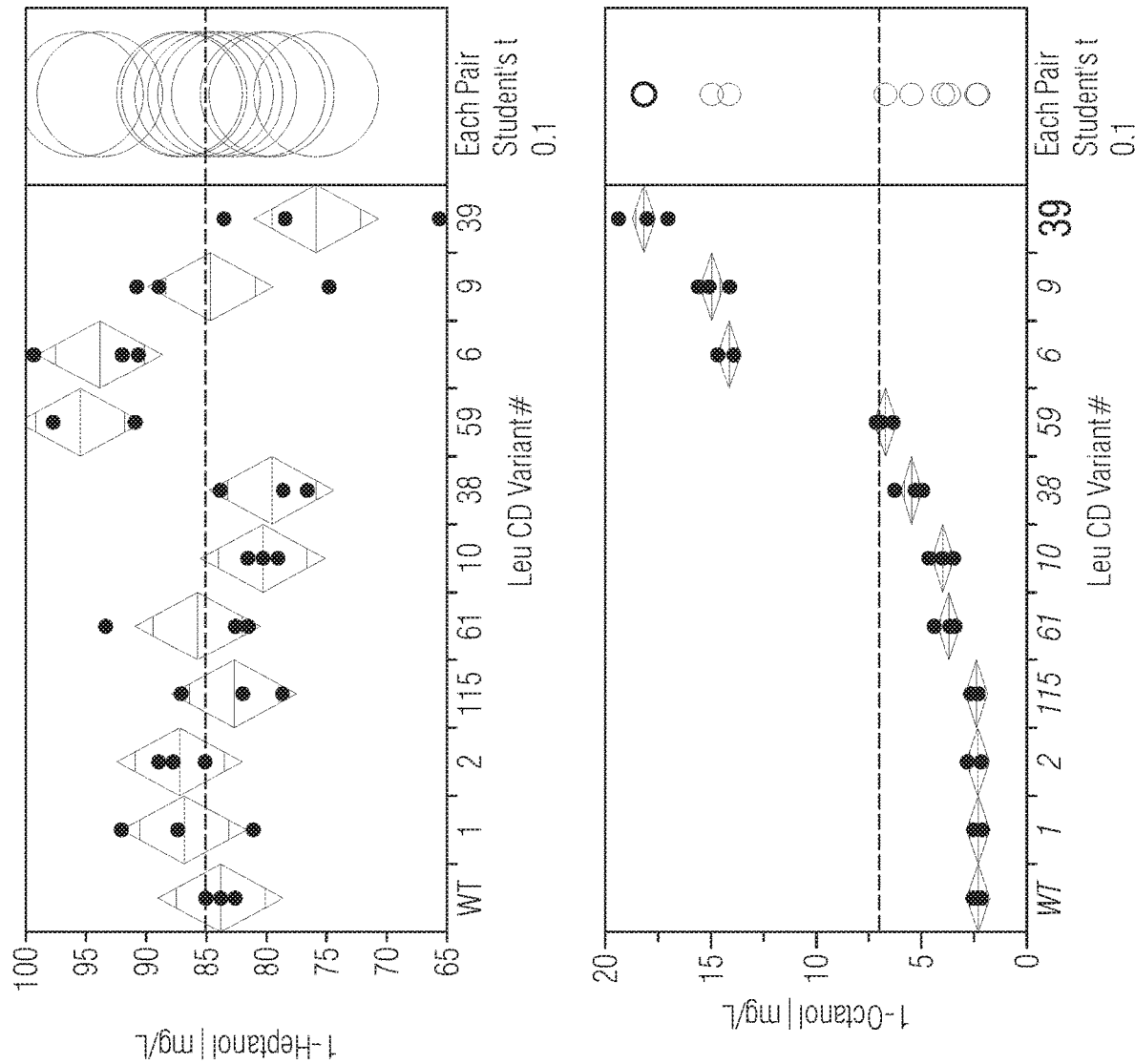

FIG. 9. Statistical analysis of alcohol titers for serum bottle fermentations of *E. coli* containing the '+1 pathway enzymes in combination with the WT and variant LeuCD enzymes. FIG. 9A shows ANOVA analyses and Student's t tests performed using SAS JMP 11.2.0 using a 90% confidence interval for the heptanol titers generated by +1 Pathway *E. coli* strains containing the WT and variant LeuC and LeuD enzymes. FIG. 9B shows ANOVA analyses and Student's t tests performed using SAS JMP 11.2.0 using a 90% confidence interval for the octanol titers generated by +1 Pathway *E. coli* strains containing the WT and variant LeuC and LeuD enzymes.

DETAILED DESCRIPTION

Reference will now be made in detail to various embodiments of genetically modified LeuCD' enzyme complexes, processes for preparing a $C_7$-$C_{11}$ 2-ketoacid utilizing genetically modified LeuCD' enzyme complexes, and microbial organisms including genetically modified LeuCD' enzyme complexes. The genetically modified LeuCD' enzyme complexes, processes for preparing a $C_7$-$C_{11}$ 2-ketoacid, and microbial organisms including genetically modified LeuCD' enzyme complexes can be used to produce bio-based chemicals and industrial products as alternatives to using fossil fuels. The instantly-disclosed genetically modified LeuCD' enzyme complexes, processes for preparing a $C_7$-$C_{11}$ 2-ketoacid, and microbial organisms including genetically modified LeuCD' enzyme complexes can be used for producing longer chain alkanes, alcohols, and carboxylic acids, both in vivo and in vitro.

As used herein, the singular forms "a." "an" and "the" include plural referents unless the context clearly dictates otherwise. Thus, for example, reference to "a" component includes aspects having two or more such components, unless the context clearly indicates otherwise.

In various embodiments, genetically modified LeuCD' enzyme complexes with isopropylmalate isomerase activity are disclosed. In certain embodiments, the genetically modified LeuCD' enzyme complexes are included in cellular extracts from cells overexpressing the genetically modified LeuCD' enzyme complexes. In embodiments, the genetically modified LeuCD' enzyme complexes include a number of altered amino acid sequences of a LeuCD enzyme complex. In embodiments, the altered amino acid sequences having been identified as exhibiting improved activity and catalytic efficiency (i.e., $k_{cat}/K_m$) at isomerizing longer chain 2-alkylmalates, such as e.g., $C_4$-$C_6$ 2-alkylmalates, to their corresponding 3-alkylmalates in comparison with the wild type *E. coli* LeuCD enzyme complex (LeuC: EcoGene Accession Number EG11576, Gene ID 945076; and LeuD: EcoGene Accession Number EB11575, Gene ID: 945642). Various sites within the wild type LeuC sequence (SEQ ID NO: 1) and wild type LeuD sequence (SEQ ID NO: 2) have been identified as key to obtaining the improvements. The sites within the wild type sequence of LeuC include Val-35, Leu-411, and combinations thereof. The sites within the wild type sequence of LeuD include Leu-31, His-88, and combinations thereof. In each alteration, changes are made wherein: alanine or glycine is substituted for Val-35 of LeuC: valine, alanine, or glycine is substituted for Leu-411 of LeuC; valine, alanine, or glycine is substituted for Leu-31 of LeuD; and/or serine or alanine is substituted for His-88 of LeuD. The substitutions can vary from single-site (i.e. single amino acid constituting three base pairs) substitution in either LeuC or LeuD, to a wide variety of multiple-site (e.g., from 2-4 sites) substitutions within both LeuC and LeuD. SEQ ID NO: 3-37 show amino acid sequences for the variations of LeuC and LeuD produced that include one or more of the substitutions as specified.

In embodiments, the genetically modified LeuCD' enzyme complexes include (a) a LeuC subunit and (b) a Leu D subunit. In some embodiments, the LeuC subunit (a) is selected from the group consisting of: (1) a native LeuC subunit including an amino acid sequence with at least 80% homology to SEQ ID NO: 1; and (2) a genetically modified LeuC subunit including an amino acid sequence with at least 80% homology to SEQ ID NO: 1 and at least one modification wherein alanine, glycine, or valine is independently substituted for Val-35. Leu-411, or a combination thereof. As the term is used herein, in some embodiments "homology" refers to identical or functional correspondence of a certain percent, or more, of the amino acids listed in the sequence, in their given positions. In other embodiments, the (1) native LeuC subunit includes an amino acid sequence with at least 90% homology to SEQ ID NO: 1, while the (2) genetically modified LeuC subunit includes an amino acid sequence with at least 90% homology to SEQ ID NO: 1 and at least one modification wherein alanine, glycine, or valine is independently substituted for Val-35, Leu-411, or a combination thereof.

In some embodiments of the genetically modified LeuCD' enzyme complexes, the LeuD subunit (b) is selected from the group consisting of: (1) a native LeuD subunit including an amino acid sequence with at least 80% homology to SEQ ID NO: 2; and (2) a genetically modified LeuD subunit including an amino acid sequence with at least 80% homology to SEQ ID NO: 2 and at least one modification wherein alanine, glycine, valine, or serine is independently substituted for Leu-31, His-88, or a combination thereof. In other embodiments, the (1) native LeuD subunit includes an amino acid sequence with at least 90% homology to SEQ ID NO: 2, while the (2) genetically modified LeuD subunit includes an amino acid sequence with at least 90% homology to SEQ ID NO: 2 and at least one modification wherein alanine, glycine, valine, or serine is independently substituted for Leu-31, His-88, or a combination thereof. In some embodiments, the LeuCD' enzyme complex includes a combination of (a)(1) and (b)(2), a combination of (a)(2) and (b)(2), or a combination of (a)(2) and (b)(1). Importantly, the genetically modified LeuCD' enzyme complex has isopropylmalate isomerase activity.

In certain embodiments of the genetically modified LeuCD' enzyme complex, at least one modification of the amino acid sequence of LeuC, (a)(2), is selected from the group consisting of: (i) alanine for Val-35; (ii) glycine for Val-35; (iii) alanine for Val-35 and valine for Leu-411; (iv) alanine for Val-35 and alanine for Leu-411; (v) alanine for Val-35 and glycine for Leu-411; and (vi) glycine for Val-35 and valine for Leu-411. In other embodiments of the genetically modified LeuCD enzyme complex, the at least one modification of the amino acid sequence of LeuD. (b)(2), is selected from the group consisting of: (i) alanine for Leu-31; (ii) glycine for Leu-31; (iii) valine for Leu-31; (iv) alanine for Lu-31 and serine for His-88; (v) glycine for Leu-31 and alanine for His-88; (vi) glycine for Leu-31 and serine for His-88; and (vii) valine for Leu-31 and alanine for His-88.

In some embodiments, the LeuCD' enzyme complex comprises a combination of (a)(1) and (b)(2), and the at least one modification of the amino acid sequence of (b)(2) is glycine for Leu-31. In other embodiments, the LeuCD' enzyme complex comprises a combination of (a)(2) and (b)(2), and the at least one modification of the amino acid sequence of (a)(2) is alanine for for Val-35, and wherein the at least one modification of the amino acid sequence of (b)(2 is glycine for Leu-31. In some embodiments, the LeuCD' enzyme complex comprises a combination of (a)(2) and (b)(2), the at least one modification of the amino acid sequence of (a)(2) is alanine for Val-35 and glycine for Leu-411, and the at least one modification of the amino acid sequence of (b)(2) is glycine for Leu-31.

As used herein, two proteins (or a region of the proteins) are substantially homologous when the amino acid sequences have a certain percentage or more identity, e.g., at least about 50% 60%, 65%, 70%, 75%, 80%, 85%, 90%, 91%, 92%, 93%, 94%, 95%, 96%, 97%, 98%, or 99% identity. Percent homology can be determined as is known in the art. For example, to determine the percent identity of two amino acid sequences, the sequences are aligned for optimal comparison purposes (e.g., gaps can be introduced in one or both of a first and a second amino acid sequence for optimal alignment and non-homologous sequences can be disregarded for comparison purposes). The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). As is known in the art, the percent identity between the two sequences is a function of the number of identical positions shared by the sequences, taking into account the number of gaps, and the length of each gap, which need to be introduced for optimal alignment of the two sequences. Sequence homology for polypeptides is typically measured using sequence analysis software.

When homologous is used in reference to proteins or peptides, it is recognized that residue positions that are not identical can often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are known to those of skill in the art. The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A). Valine (V), and 6) Phenylalanine (F), Tyrosine (Y), Tryptophan (W).

For example, amino acid sequences having the function of LeuC or LeuD can be identified by performing a protein-protein BLAST (blastp) search of the non-redundant protein sequences (nr) database using the amino acid sequences of these proteins as query. The search can be conducted on the National Center for Biotechnology Information (NCBI) website (blast.ncbi.nlm.nih.gov) using default parameters. An alignment of amino acid sequences of the large subunit of isopropylmalate isomerases that diverged from the E. coli LeuC sequence by as much as 1-60%, showed that more than 80% of sequences had the shown 284 amino acid residues (shown as shaded sequence in FIG. 4). Based on these observations, residues that are shaded in FIG. 4 may be considered necessary amino acid residues for conferring LeuC function (that includes folding of the enzyme, substrate binding, specificity, catalysis etc) in the same way as it does in E. coli LeuC. Additionally. and without being bound by the theory, it is believed that the active site of isopropylmalate isomerase (LeuCD) includes the following amino acid residues of the large subunit (LeuC) thereof: V32-S37, D62-N64, G106-V110, G127-T131, C220-M222, G345-T348, G406-A412, S428-N431, and G434-Q436 (shown as boxed in FIG. 4).

Similarly, an alignment of amino acid sequences of the small subunit of isopropylmalate isomerases that diverged from the E. coli LeuD sequence by as much as 60%, showed that mom than 80% of sequences had the shown 101 amino acid residues (shown as shaded sequence in FIG. 5). Based on these observations, residues that are shaded in FIG. 5 may be considered necessary amino acid residues for conferring LeuD function (that includes folding of the enzyme, substrate binding, specificity, catalysis etc) in the same way as it does in E. coli LeuD. Additionally and without being bound by the theory, it is believed that the active site of isopropylmalate isomerase (LeuCD) includes the following amino acid residues from the small subunit (LeuD) thereof: T22-D23, P27-L31, and G83-E87 (shown as the boxed regions in FIG. 5).

In embodiments, amino acid residues which are not believed to be essential for the functioning of isopropylmalate isomerase (e.g., residues that are not shaded in FIG. 4 for Leu C, and residues that are not shaded in FIG. 5 for LeuD) may be substituted either conservatively or nonconservatively, and such amino acid substitutions would not significantly diminish the functional properties of the modified isopropylmalate isomerase as compared to wild-type *E. Coli* LeuCD. In embodiments, amino acid residues which are not believed to form the active site of isopropylmalate isomerase but are still considered necessary amino acid for the functioning of isopropylmalate isomerase (e.g., residues that are shaded but not boxed in FIG. 4 for LeuC and residues that are shaded but not boxed in FIG. 5 for Leu 5) may be conservatively substituted, and such amino acid substitutions would not significantly diminish the functional properties of the modified isopropylmalate isomerase as compared to wild-type *E. Coli* LeuCD. In embodiments, most conservative and nonconservative amino acid substitutions for amino acid residues which are believed form the active site of isopropylmalate isomerase (e.g., residues that are shaded and boxed in FIG. 4 for LeuC and residues that are shaded and boxed in FIG. 5 for LeuD), other than those specific amino acid substitutions described herein, will likely diminish the functional properties of the modified isopropylmalate isomerase as compared to wild-type *E. coli* LeuCD. It is believed that genetically modified large and/or small subunits of isopropylmalate isomerase having the described substitutions would confer isopropylmalate isomerase activity. Stated another way, it is believed that the amino acid substitutions described herein would not significantly diminish the functional properties of the modified isopropylmalate isomerase as compared to wild-type *E. Coli* LeuCD.

The instantly disclosed genetically modified LeuCD' enzyme complexes with the improved properties over the wild type LeuCD enzyme complex of *E. coli*, e.g., improved activity and catalytic efficiency (i.e., $k_{cat}/K_m$) at isomerizing longer chain 2-alkylmalates such as $C_5$-$C_6$ 2-alkylmalates, may be created through genetic modification in one of a variety of ways that are described herein. The terms "genetically modified." or "modified." as used herein, refer to the group of instantly disclosed genetically modified LeuCD' enzyme complexes having an intentionally altered amino acid sequence, i.e., a "non-wild type" amino acid sequence, or to a microbial organism (depending upon placement of either term as an adjective) having a genome that has been intentionally altered as to (at least) the specific, modified LeuCD' enzyme complex(es) described herein, or both. Such alterations may be accomplished via recombinant technology, wherein one or more genes is transferred from a second, different microbial organism into a target microbial organism. Recombinant technology can be accomplished using fully synthetic DNA that is transferred to the target microbial organism using conventional methods. Such alterations may also be accomplished via engineered technology, wherein the nucleic acids within the target microbial organism are altered, generally via site-directed mutagenesis, resulting in the conversion of at least one nucleic acid to a different nucleic acid and therefore modification of one or more enzymes. Combinations of any of the above methods and those described throughout the application may also be employed. Thus, it will be understood that the instantly disclosed genetically modified LeuCD' enzyme complexes can be used either in vivo. i.e., by a genetically modified microbial organism, or in vitro.

In embodiments, processes for preparing a $C_7$-$C_{11}$ 2-ketoacid are provided. In embodiments, the processes for preparing $C_7$-$C_{11}$ 2-ketoacids include providing at least one of a $C_4$-$C_{10}$ 2-ketoacid substrate with a series of enzymes that include a genetically-modified LeuCD enzyme complex. In some embodiments, the processes include preparing a $C_7$-$C_{11}$ 2-ketoacid by providing a starting substrate and a series of enzymes that act on the substrate or product thereof. In embodiments, the series of enzymes include a genetically-modified LeuCD enzyme complex of the instant disclosure. In some embodiments, the series of enzymes ultimately convert the substrate, to the desired $C_7$-$C_{11}$ 2-ketoacid. As used herein, the terms "substrate" or "suitable substrate" refer to any substance or compound that is converted or meant to be converted into another compound by the action of an enzyme. The term includes not only a single compound, but also combinations of compounds, such as solutions, mixtures and other materials which contain at least one substrate, or derivative thereof. Further, the term "substrate" encompasses not only compounds that provide a carbon source suitable for use as a starting material, such as e.g., any biomass derived sugar, but also intermediate and end product metabolites used in a pathway associated with a metabolically engineered microbial organism as described herein.

In some embodiments, the processes for preparing a $C_7$-$C_{11}$ 2-ketoacid further include converting the $C_7$-$C_{11}$ 2-ketoacid, with even further additional enzymes and biochemical reactions, to a desired $C_6$-$C_{10}$ aldehyde, $C_6$-$C_{10}$ alcohol, $C_6$-$C_{10}$ carboxylic acid, or $C_5$-$C_9$ alkane. These processes may be carried out biosynthetically in one of the described embodiments of a non-naturally occurring, i.e., genetically engineered, cell. For example, in illustrative, non-limiting embodiments, these processes may be carried out in a non-naturally occurring microbial organism. Alternatively, in other illustrative, non-limiting embodiments, production of the $C_7$-$C_{11}$ 2-ketoacid(s), $C_6$-$C_{10}$ aldehyde(s), $C_6$-$C_{10}$ alcohol(s), $C_6$-$C_{10}$ carboxylic acid(s), or $C_5$-$C_9$ alkane(s) may be carried out via in vitro methodology, typically beginning from a starting point that does not include a microbial organism.

Figure 1:
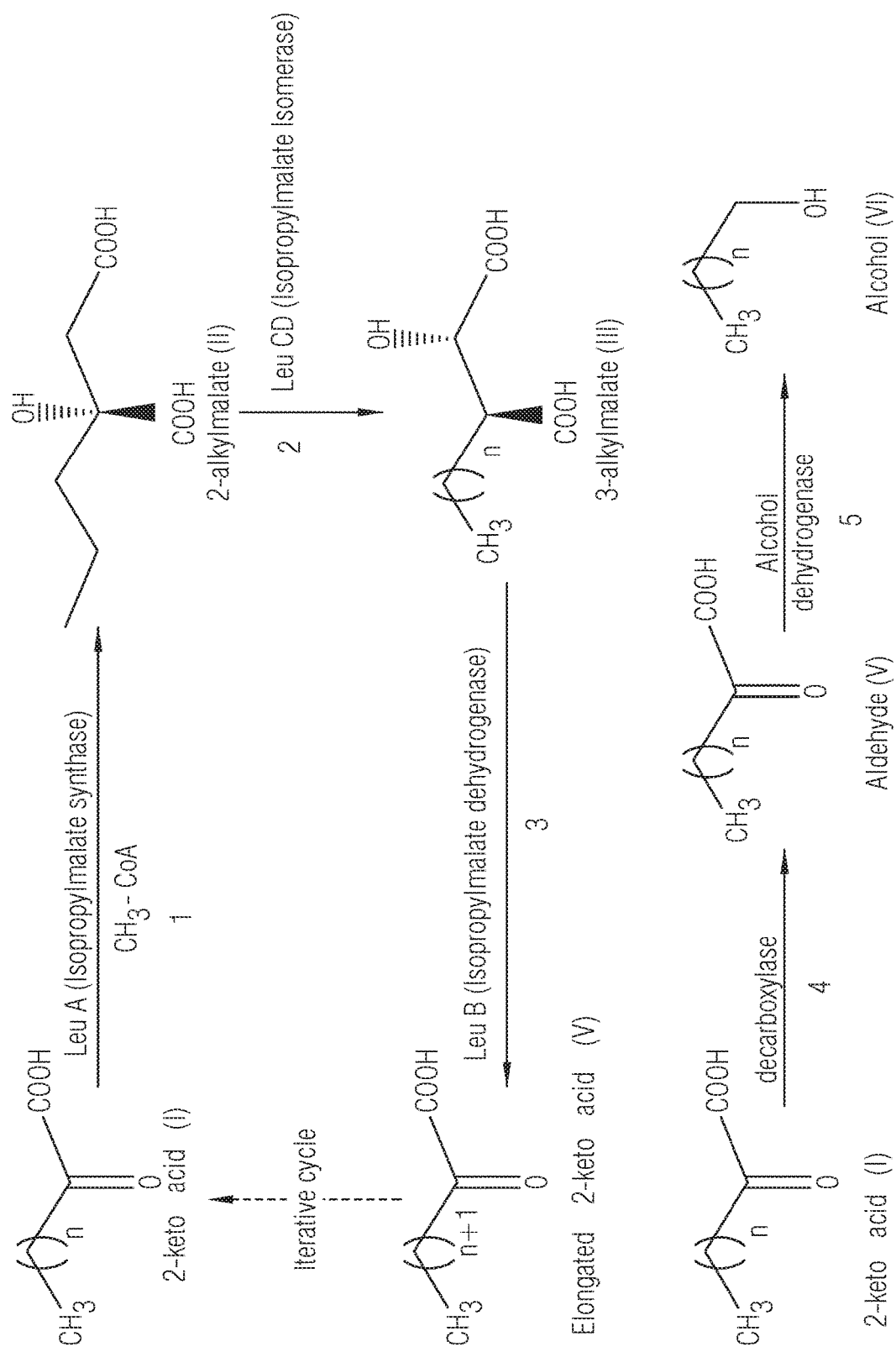
FIG. 1. Elongation of a 2-ketoacid.
Figure 2:
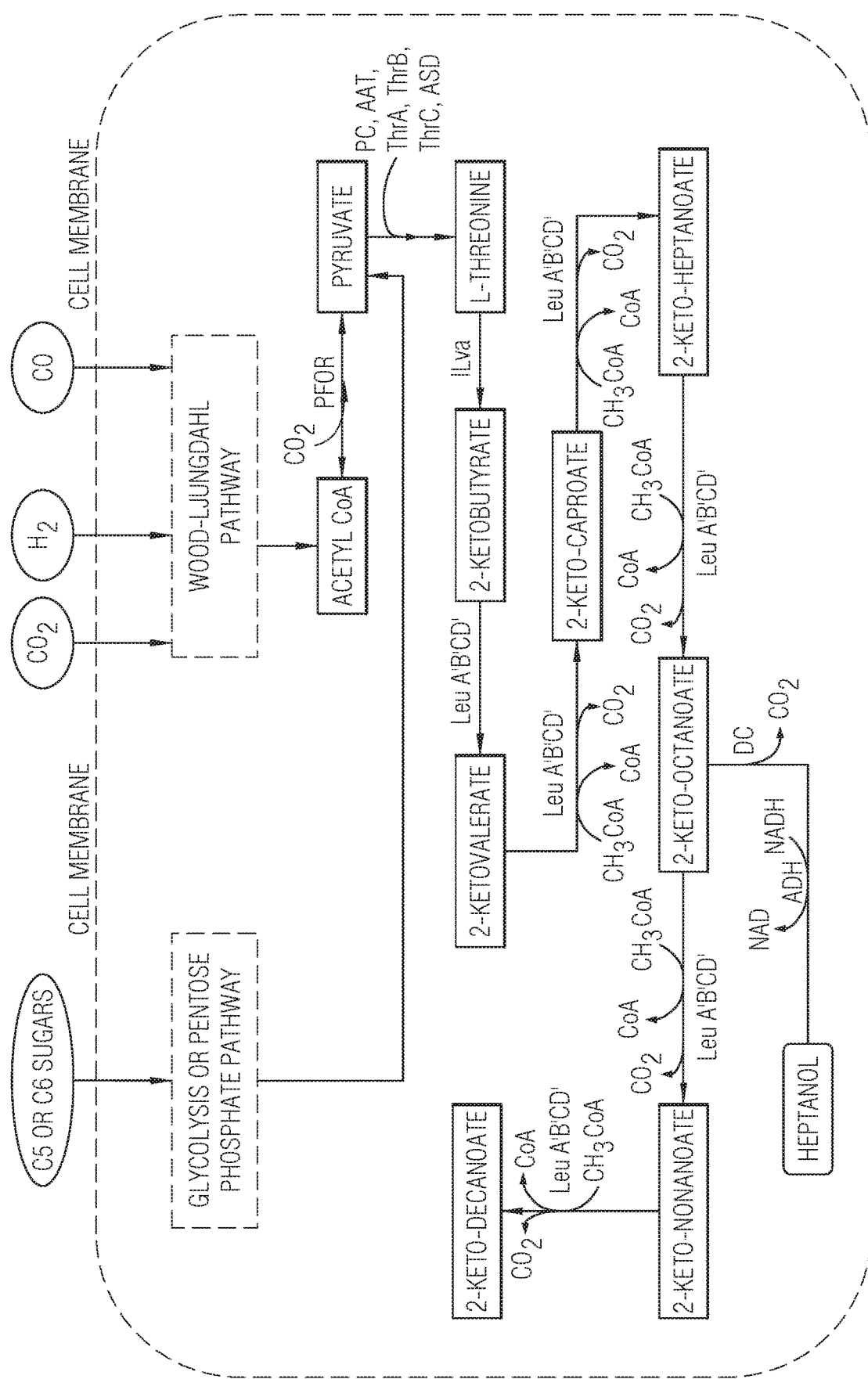
FIG. 2. Two pathways to produce 1-heptanol.
Figure 3:
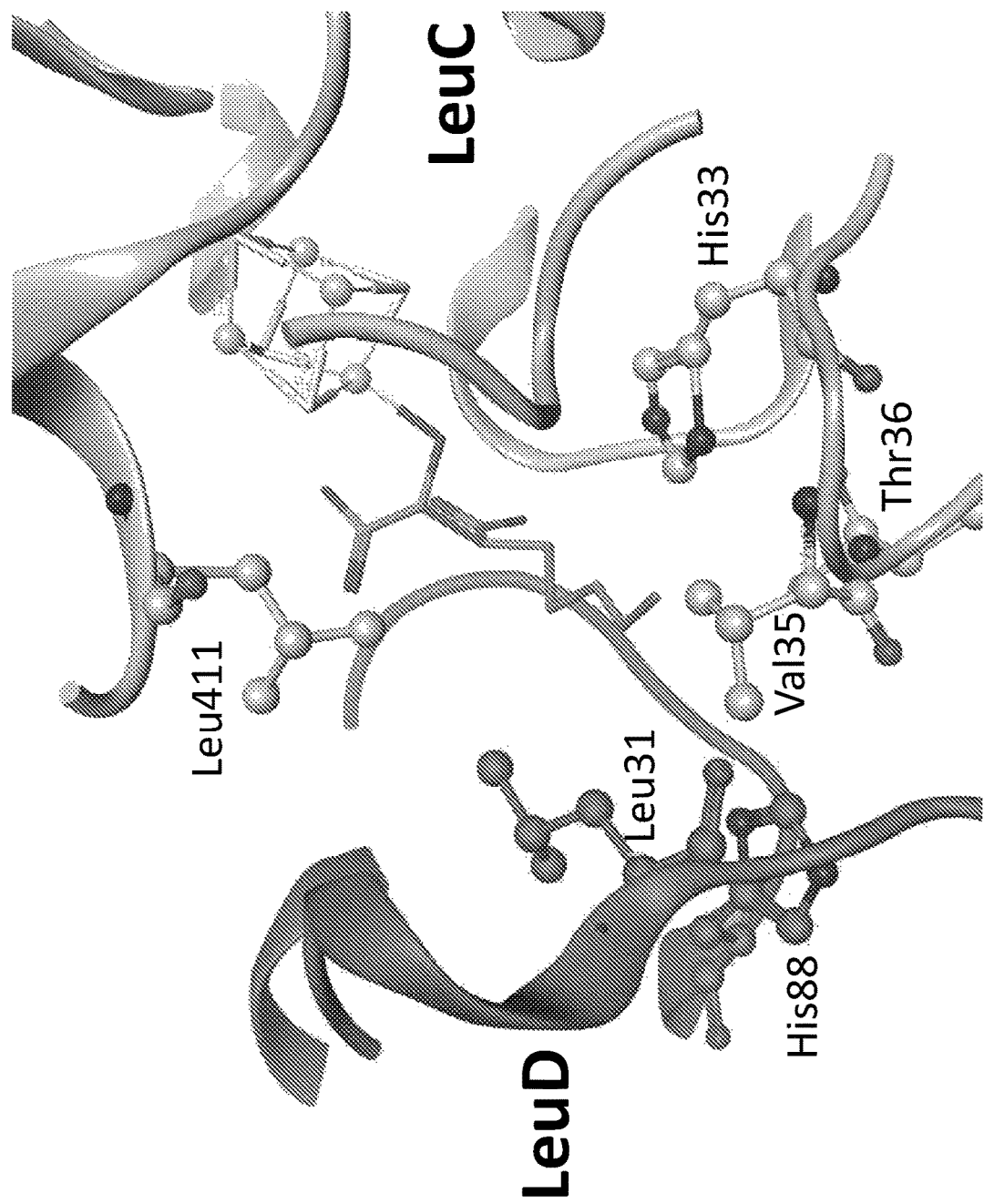
FIG. 3. Homology model of the LeuCD active site.

In some embodiments of the processes to prepare the $C_7$-$C_{11}$ 2-ketoacid(s), $C_6$-$C_{10}$ aldehyde(s). $C_6$-$C_{10}$ alcohol(s). $C_6$-$C_{10}$ carboxylic acid(s), or $C_5$-$C_9$ alkane(s), a selected carbon-containing substrate is converted first to pyruvate, and from pyruvate to either 2-ketobutyrate or, alternatively, to 2-ketoisovalerate, via the action of one or more enzymes and in one or more biochemical reactions (FIG. 2). More specifically, in embodiments, the carbon-containing substrate is provided and/or contacted with one or more enzymes in one or more biochemical reactions such that it is converted to 2-ketobutyrate, 2-ketoisovalerate, or 2-methyl-2-ketopentanoate. The 2-ketobutyrate, 2-ketoisovalerate, or 2-methyl-2-ketopentanoate may then be converted, via chain elongation, to a $C_7$-$C_{11}$, 2-ketoacid, by the action of the enzymes, enzyme complexes, genetically modified enzymes, genetically modified enzyme complexes, or a combination thereof in the "+1" pathway (or the LeuABCD pathway, as it is termed with respect to the *E. coli* microbial organism). The iterative part of the "+1" pathway (or the iterative part of the LeuABCD pathway in *E. coli*) is a portion of the non-natural leucine pathway (FIG. 1). In embodiments, the enzymes capable of accomplishing this chain elongation are identified herein as constituting: isopropylmalate synthase (e.g., a native 2-isopropylmalate synthase such as LeuA (GenBank:Accession No. NC 000913.3 Gene ID: 947465), and/or a genetically modified isopropylmalate synthase having isopropylmalate synthase activity, such as LeuA', (e.g., as described by Marcheschi et. al. A synthetic recursive "+1" pathway for carbon chain elongation. ACS chemical biology 2012, 7, 689-697, which is incorporated by reference in its entirety)); isopropylmalate dehydrogenase (e.g., a native isopropylmalate dehydrogenase, such as LeuB (GenBank:Accession NO. NC 000913.3 Gene ID: 944798), and/or a genetically modified isopropylmalate dehydrogenase having isopropylmalate dehydrogenase activity, such as LeuB' (e.g., as described by Sanghani et al in WO2015089127A1, which is incorporated by reference in its entirety)); and/or a LeuCD complex (e.g., a native LeuCD complex (i.e., two enzymes that, together, are termed isopropylmalate isomerase complex) (GenBank: Accession No. NC 000913.3 Gene ID: 945076 and Gene ID: 945642, respectively), and/or a genetically modified LeuCD', as described above). In embodiments, the genetically modified LeuCD' complex is as previously described hereinabove. The appropriate substrates, including intermediates and end product metabolites may be added at any point in the LeuABCD pathway (shown in FIG. 1) as would be known to one of ordinary skill in the art.

In embodiments, the genetically modified isopropylmalate synthase having isopropylmalate synthase activity can be as previously described above, and/or as described by Marcheschi et. al. A synthetic recursive "+1" pathway for carbon chain elongation. ACS chemical biology 2012, 7, 689-697, which is incorporated by reference in its entirety. In certain embodiments, the genetically modified isopropylmalate synthase having isopropylmalate synthase activity can comprise a LeuA' variant having substitutions at one or more amino acid residue sights designated Phe-47 Leu-73, His-97, Phe-99, Ser-139, Asn-167, Pro-169, Asn-197, and/or Gly-462. One or more of these targeted amino acids is/are then substituted with the amino acids glycine, alanine, leucine, and/or valine, which can be performed by site-directed mutagenesis of the known isopropylmalate synthase of a selected organism, such as the LeuA gene of $E.$ $coli$ (GenBank: Accession No. NC_000913.3 Gene ID:947465). In certain aspects, the genetically modified LeuA' can include the following combination of substitutions: alanine for His-97, glycine for Ser-139, glycine for Asn-167, alanine for Pro-169, and/or aspartic acid for Gly-462. These genetically modified LeuA' variants are more efficient (higher $k_{cat}/K_m$) than the wild type enzyme in capturing 2-ketoacids of interest for catalysis, and thus can improve the overall efficiency of the relevant "+1" pathway In embodiments, the genetically modified isopropylmalate dehydrogenase having isopropylmalate dehydrogenase activity can be as described by Sanghani et al in WO2015089127A1, which is incorporated by reference in its entirety. In certain embodiments, the genetically modified isopropylmalate dehydrogenase having isopropylmalate dehydrogenase activity can comprise a LeuB' variant having substitutions at one or more amino acid residue sights designated Leu-96 and Val-198. One or more of these targeted amino acids is/are then substituted with the amino acids glycine, alanine, and/or valine, which can be performed by site-directed mutagenesis of the known isopropylmalate dehydrogenase of a selected organism, such as the LeuB gene of $E.$ $coli$ (GenBank:Accession No. NC_000913.3 Gene ID: 944798). In certain aspects, the genetically modified LeuB' can include the following substitutions: glycine for Leu-96; alanine for Val-198; alanine for Leu-96 and alanine for Val-198; glycine for Leu-96 and alanine for Val-198; glycine for Leu-96 and glycine for Val-198'; or alanine for Leu-96. These genetically modified LeuB' variants are more efficient (higher $k_{cat}/K_m$) than the wild type enzyme in converting 3-HM to the corresponding $C_7$-$C_{11}$ 2-ketoacid, and thus can improve the overall efficiency of the relevant "+1" pathway Following chain elongation of the 2-ketobutyrate, 2-ketoisolvalerate, or 2-methyl-2-ketopentanoate the $C_7$-$C_{11}$ 2-ketoacid may then be converted to a $C_6$-$C_{10}$ aldehyde by the action of at least one enzyme, such as, a thiamin dependent decarboxylase (e.g., a native and/or genetically modified thiamin dependent decarboxylase having decarboxylase activity). Specifically, the 2-ketobutyrate, 2-ketoisovalerate, or 2-methyl-2-ketopentanoate may be provided and/or contacted with a native and/or genetically modified thiamin dependent decarboxylase having decarboxylase activity. In embodiments wherein a native and/or genetically modified thiamin dependent decarboxylase acts on the $C_7$-$C_{11}$ 2-ketoacid, the native and/or genetically modified thiamin dependent decarboxylase converts the $C_7$-$C_{11}$ 2-ketoacid to a $C_6$-$C_{10}$ aldehyde having one less carbon atom than the $C_7$-$C_{11}$ 2-ketoacid being converted. In embodiments, the thiamin dependent decarboxylase has thiamin dependent decarboxylase activity. Further disclosure regarding the modification and selection of thiamin dependent decarboxylase having thiamin dependent decarboxylase activity is included in co-pending International Publication Number WO 2015/089127, which is incorporated herein in its entirety by reference.

The $C_6$-$C_{10}$ aldehyde(s) may be used as is, in a variety of industrial applications, or may be employed as an intermediate and/or starting material for production of other chemicals. For example, the $C_6$-$C_{10}$ aldehyde(s) may be provided and/or contacted with an alcohol dehydrogenase (e.g., a native (Accession No. NC_001145.3, GeneID:855368) and/or genetically modified alcohol dehydrogenase) which converts the $C_6$-$C_{1a}$ aldehyde to the corresponding $C_6$-$C_{10}$ alcohol. In embodiments, the alcohol dehydrogenase has alcohol dehydrogenase activity. Alternatively, the $C_6$-$C_{10}$ aldehyde(s) may be provided and/or contacted with an aldehyde dehydrogenase (e.g., a native and/or genetically modified aldehyde dehydrogenase (Accession No. NM_000689.4)) which converts it to the corresponding $C_6$-$C_{10}$ carboxylic acid. In embodiments, the aldehyde dehydrogenase has aldehyde dehydrogenase activity. Finally, the $C_6$-$C_{10}$ aldehyde(s) may be contacted with a fatty aldehyde decarbonylase (e.g., a native and/or genetically modified fatty aldehyde decarbonylase (Accession No. NM_100101.3)) which converts it to the corresponding $C_{n-1}$ alkane. In embodiments, the fatty aldehyde decarbonylase has fatty aldehyde decarbonylase activity.

In preferred embodiments, the $C_6$-$C_{10}$ product, for example, a $C_6$-$C_{10}$ alcohol, a $C_6$-$C_{10}$ carboxylic acid, or a $C_5$-$C_9$ alkane is produced with desirably high specificity. This high specificity can be, e.g., preferably at least 25 percent (i.e., %), more preferably at least 40%, still more preferably at least 50%, and most preferably at least 70%, based on weight (i.e., wt) of total product (i.e., wt %), as the targeted product.

As noted hereinabove, the processes described herein may be carried out either in vivo or in vitro. An in vivo approach may be preferred for commercial scale production, although in some cases an in vitro approach may be suitable for commercial scale production. In embodiments, an in vitro approach may be particularly convenient for laboratory and general research purposes, such as, e.g., to carry out enzymatic assays. For example, desirable microbial organisms useful for large or commercial scale fermentative production of an enzyme-facilitated product, such as a $C_6$-$C_{10}$ alcohol or combination of $C_6$-$C_{10}$ alcohols, may be prepared. Such preparation may be carried out by inserting the DNA, or pieces of DNA, which encode the desired enzyme, from a first microbial organism into the genome of a second, microbial organism. In embodiments, the host microbial organism is known or believed to possess one or more desired metabolic pathways and/or other desired features, such as resistance to growth inhibition by the $C_6$-$C_{10}$ product, using recombinant technology. In general, the in vivo approach employs a microbial organism's wild type metabolic pathway(s), first to convert a suitable carbon-containing substrate to pyruvate, and then to convert the pyruvate to 2-ketobutyrate, 2-ketoisovalerate, or 2-methyl-2-ketopentanoate in a varying number of biochemical reactions.

For example, the instantly disclosed genetically modified LeuCD' enzyme complexes may be used and/or expressed as part of a metabolic pathway in a microbial organism that produces acetyl coA via either an anabolic (e.g., Wood-Ljungdahl) or catabolic (e.g., glycolysis, or a pentose phosphate pathway) route (FIG. 2). The $C_7$-$C_{11}$ 2-ketoacid may then be converted to the corresponding $C_6$-$C_{10}$ aldehyde having one less carbon by the action of at least one more enzyme, such as, e.g., a thiamin dependent decarboxylase (e.g., a native and/or genetically modified thiamin dependent decarboxylase having decarboxylase activity). In some embodiments, the $C_6$-$C_{10}$ aldehyde may be further reacted with appropriate enzymes to form a $C_6$-$C_{10}$ alcohol. $C_6$-$C_{10}$ carboxylic acid, or a corresponding $C_{5-9}$ alkane. Because of the specific alterations in its amino acid sequence that are described herein, the genetically modified LeuCD' enzyme complexes described herein offer some significant differences in specificity to various substrates, and this alteration in specificity offers important advantages in terms of product yields and the reduction or elimination of undesirable and/or competing side products. For example, the genetically modified LeuCD' enzyme complexes exhibit improved activity and catalytic efficiency (i.e., $k_{cat}/K_m$) at isomerizing longer chain 2-alkylmalates, such as $C_4$-$C_6$ 2-alkylmalates, to their corresponding 3-alkylmalates in comparison with the wild type E. coli LeuCD enzyme complex.

In some embodiments, the selected microbial organism may possess a Wood-Ljungdahl pathway, also known as a "synthesis gas (syngas) fixation pathway," wherein syngas is converted to acetyl CoA, as shown in FIG. 2. Such may be carried out by certain acetate-producing bacteria species, such as those of the genus Clostridium, including but not limited to, in particular, Clostridium ljungdahlii (i.e., C. ljungdahlii). In the Wood-Ljungdahl pathway, conversion of the syngas to acetyl CoA generally includes reduction of carbon dioxide to carbon monoxide, and then to acetyl CoA via the action of two enzymes, carbon monoxide dehydrogenase and acetyl CoA synthase. Carbon monoxide dehydrogenase, which catalyzes the reduction of the carbon dioxide, and acetyl CoA synthase, which combines the resulting carbon monoxide with a methyl group to form acetyl CoA. From this point the acetyl CoA continues on another pathway wherein it is converted to pyruvate via reduction by PFO (i.e., ferrodoxin oxidoreductase). In alternative embodiments, a suitable (e.g., a non-syngas) carbon-containing substrate, such as e.g., a $C_5$ or $C_6$ sugar (e.g., glucose, sucrose, pentose, or a combination thereof), may be converted directly to pyruvate via one of the sugar catabolism pathways, such as a glycolysis or pentose phosphate pathway, as shown in FIG. 2. Such pathways may be present in microbial organisms including, for example, Clostridium, Escherichia coli (i.e., E. coli). Azospirillum, Bacillus. Saccharomyces, and Corynebacterium.

Upon conversion of the syngas or non-syngas substrate to pyruvate, the pyruvate may be converted first to L-threonine, via PC (i.e., pyruvate carboxylase); AAT (i.e., aspartate aminotransferase); ThrABC (which includes: ThrA, which is a bifunctional aspartokinase/homoserine dehydrogenase; ThrB, which is homoserine kinase; and ThrC, which is threonine synthase); and ASD (i.e., aspartate semialdehyde dehydrogenase). The L-threonine may then be converted to 2-ketobutyrate via llva (i.e., threonine dehydratase). In an alternative embodiment, the pyruvate may be converted to 2-ketoisovalerate via the activities of llvBN/llvGM, llvC, and llvD. In certain embodiments, the pyruvate may be converted to 2-methyl-2-keto pentanoate in a varying number of biochemical reactions.

Following production of 2-ketobutyrate, 2-ketoisovalerate, or 2-methyl-2-keto pentanoate, genetic modification of the native "+l" pathway portion (or the native LeuABCD portion in E. coli) of the leucine biosynthesis pathway operates to effect conversion to a $C_7$-$C_{11}$ 2-ketoacid via one or more biochemical reactions. In an in vivo approach, several biochemical reactions are involved and employ at least one native or modified (i.e., endogenous or exogenous) enzyme, enzyme complex, or combination thereof (with the genetically modified enzymes or enzyme complexes of the LeuABCD pathway collectively referred to herein as "Leu A', Leu B', and Leu CD'", and the native enzymes and enzyme complexes of the LeuABCD pathway termed "LeuA, LeuB, LeuC, and LeuD"). In embodiments, the native and/or genetically modified enzymes of the LeuABCD pathway, converts 2-ketobutyrate, 2-ketoisovalerate, or 2-methyl-2-keto pentanoate to a desired $C_7$-$C_{11}$ 2-ketoacid (FIG. 1). For example, in embodiments, 2-ketobutyrate is converted first to 2-ketovalerate, then to 2-ketocaproate, then to 2-ketoheptanoate or up to 2-ketoundecanoate, i.e., a desired $C_7$-$C_{11}$ 2-ketoacid depending upon the desired final product, as chain-lengthening occurs through the recursive pathway. In alternative embodiments, 2-ketoisovalerate is converted first to 2-ketoisocaproate, then to 2-ketoisoheptanoate, and so forth. The native enzymes and/or genetically modified enzymes accomplishing this chain elongation may include 2-isopropylmalate synthase (e.g., a native 2-isopropylmalate synthase such as native LeuA and/or a genetically modified 2-isopropylmalate synthase having isopropylmalate synthase activity such as genetically modified LeuA' having isopropylmalate synthase activity), an isopropylmalate dehydrogenase (e.g., a native isopropylmalate dehydrogenase such as native LeuB and/or a genetically modified isopropylmalate dehydrogenase having isopropylmalate dehydrogenase activity such as LeuB' having isopropylmalate dehydrogenase), and/or an isopropylmalate isomerase (e.g., a native isopropyl malate isomerase such as native LeuCD and/or a genetically modified isopropylmalate isomerase having isopropylmalate isomerase activity such as LeuCD' having isopropylmalate isomerase activity). In some embodiments, only one enzyme, enzyme complex or combination thereof is genetically modified. For example, in specific embodiments, only LeuCD' is genetically modified to obtain acceptable and/or desirable production of a $C_7$-$C_{11}$ 12-ketoacid beginning with 2-ketobutyrate or 2-ketoisovalerate.

Further disclosure regarding modification of this portion of the non-natural leucine biosynthesis pathway is included in co-pending International WO2015089127, which is incorporated herein in its entirety by reference. In certain embodiments, a genetically modified LeuA (i.e., LeuA'), a genetically modified LeuB (i.e., LeuB'), a genetically modified LeuCD' (i.e., LeuCD', as previously described herein) or combinations thereof can be utilized, as described in the referenced patent application. For example, LeuA (GenBank Accession No. NC_000913.3 Gene ID: 947465) can be genetically modified to produce an isopropylmalate synthase variant (LeuA') having a higher-than-average catalytic efficiency (kcat/Km) for capturing 2-ketoacids of interest for catalysis. In certain embodiments, a native Leu A, a genetically modified Leu A', a native LeuB, a genetically modified LeuB, a native LeuCD, and a genetically modified LeuCD' are utilized in combination.

Once an elongated $C_7$-$C_{11}$ 2-ketoacid is formed, such may be used as is, or converted to a $C_6$-$C_{10}$ aldehyde. For such conversion, a native or genetically modified thiamin dependent decarboxylase is employed, resulting in a $C_6$-$C_{10}$ aldehyde having one less carbon atom than the $C_7$-$C_{11}$ 2-ketoacid being converted. $C_6$-$C_{10}$ aldehydes have wide applicability, such as, e.g., as starting substrates or intermediates in producing $C_6$-$C_{10}$ alcohols. $C_6$-$C_{10}$ carboxylic acids, $C_5$-$C_9$ alkanes, and combinations thereof, as described hereinabove. Production of a $C_6$-$C_{10}$ alcohol is illustrated in FIG. 1.

In order to enable a non-native organism to carry out some portion of the conversions in vivo as defined hereinabove, for example, to produce the $C_7$-$C_{11}$ 2-ketoacid(s), $C_6$-$C_{10}$ aldehyde(s), $C_6$-$C_{10}$ alcohol(s), $C_6$-$C_{10}$ carboxylic acid(s), or $C_5$-$C_9$ alkane(s), it is desirable to perform protocols similar to that described herein. In general, the working examples show genetic modification involving engineering to alter one or more nucleic acid base(s) in a given codon in order to alter the amino acid which the codon encodes. Such may be used simply to produce the modified enzyme for, e.g., in vitro assay purposes. In contrast, the genome of a host microbial organism may be preferably altered for a larger scale production strain.

The following methodology, designed for in vitro enzyme production, may be carried out as is generally understood by those skilled in the art. In general, a suitable database, such as GenBank, is used to obtain the genetic codes for the wild type enzyme(s), followed by identification of the codons suitable for modification. This identification may be used as the basis for art-known methods of protein engineering, wherein computer molecular modeling identifies and also enables differentiation of structural locations at which modifications of enzyme/substrate interfaces may be effectively employed. A given desirable modification is then performed, using a molecular biology technique wherein the alteration(s) of the nucleic acid base(s) is/are done via site-directed mutagenesis. The variant-type enzymes can then be produced using recombinant methods in a suitable host such as E. coli, isolated from the cell, and can used as a whole cell extract exhibiting a higher-than-wild type catalytic efficiency. Alternately, the variant enzyme can be subjected to purification to separate out non-targeted proteins, leaving a purified enzyme that will exhibit a higher-than-wild type catalytic efficiency. This can be appropriately assayed in vitro, according to the methodology most suitable for the given particular enzyme. An assayed enzyme that is shown to have a desirable level of catalytic efficiency is thereby confirmed to be the product of a desirable genetic modification, and may be used for in vitro production methods, such as e.g., for the in vitro production and/or conversion of a given $C_7$-$C_{11}$ 2-ketoacid (such as e.g., 2-ketononoate). $C_6$-$C_{10}$ aldehyde (such as e.g., octanal), and/or a product made from the $C_6$-$C_{10}$ aldehyde (such as e.g., a $C_6$-$C_{10}$ alcohol, carboxylic acid, or a $C_5$-$C_9$ alkane).

In some embodiments a process for preparing a $C_7$-$C_{11}$ 2-ketoacid includes: (I) providing at least one of a $C_4$-$C_{10}$ 2-ketoacid substrate with (A) at least one isopropylmalate synthase having isopropylmalate synthase activity (e.g., a native 2-isopropylmalate synthase (such as native LeuA) and/or a genetically modified 2-isopropylmalate synthase (such as a genetically modified LeuA') having isopropylmalate dehydrogenase activity, (B) at least one isopropylmalate dehydrogenase having isopropylmalate dehydrogenase activity (e.g., a native isopropylmalate dehydrogenase (such as native LeuB) and/or genetically modified isopropylmalate dehydrogenase (such as a genetically modified LeuB') having isopropylmalate dehydrogenase activity), and (C) at least one genetically modified LeuCD' enzyme complex having isopropylmalate isomerase activity, under conditions that the at least one of the $C_4$-$C_{10}$ 2-ketoacid substrate is converted to the $C_7$-$C_{11}$ 2-ketoacid. In some embodiments, the process can further include a native LeuCD enzyme complex. In some embodiments, the conversion of the least one $C_4$-$C_{10}$ 2-ketoacid substrate to the $C_7$-$C_{11}$ 2-ketoacid occurs via one or more biochemical reactions. The biochemical reactions may independently occur within or outside of a genetically modified microbial organism. In certain embodiments, the $C_4$-$C_{10}$ 2-ketoacid substrate includes 2-ketobutyrate. In other embodiments, the $C_4$-$C_{10}$ 2-ketoacid substrate includes 2-ketoisovalerate. In even further embodiments, the the $C_4$-$C_{10}$ 2-ketoacid substrate includes 2-methyl-2-ketopentanoate.

In some embodiments of a process for preparing a $C_7$-$C_{11}$ 2-ketoacid, the at least one genetically modified LeuCD' enzyme complex includes (1) a LeuC subunit and (2) a LeuD subunit. In some embodiments, the LeuC subunit (1) is selected from the group consisting of: (i) a native LeuC subunit including an amino acid sequence with at least 80% homology to SEQ ID NO: 1; and (ii) a genetically modified LeuC' subunit including an amino acid sequence with at least 80% homology to SEQ ID NO: 1 and at least one modification wherein alanine, glycine, or valine is independently substituted for Val-35, Leu-411, or a combination thereof. In certain embodiments, the LeuC subunit (1) is selected from the group consisting of: (i) a native LeuC subunit including an amino acid sequence with at least 90% homology to SEQ ID NO: 1; and (ii) a genetically modified LeuC' subunit including an amino acid sequence with at least 90% homology to SEQ ID NO: 1 and at least one modification wherein alanine, glycine, or valine is independently substituted for Val-35. Leu-411, or a combination thereof. In some embodiments, LeuD subunit (2) is selected from the group consisting of: (i) a native LeuD subunit including an amino acid sequence with at least 80% homology to SEQ ID NO: 2; and (ii) a genetically modified LeuC' subunit including an amino acid sequence with at least 80% homology to SEQ ID NO: 2 and at least one modification wherein alanine, glycine, valine, or serine is independently substituted for Leu-31, His-88, or a combination thereof. In certain embodiments, LeuD subunit (2) is selected from the group consisting of: (i) a native LeuD subunit including an amino acid sequence with at least 90% homology to SEQ ID NO: 2; and (ii) a genetically modified LeuD' subunit including an amino acid sequence with at least 90% homology to SEQ ID NO: 2 and at least one modification wherein alanine, glycine, valine, or serine is independently substituted for Leu-31. His-88, or a combination thereof. The LeuC, LeuC', LeuD, and LeuD' subunits may be as previously described hereinabove.

In some embodiments of a process for preparing a $C_7$-$C_{11}$ 2-ketoacid, the at least one genetically modified LeuCD' enzyme complex includes: a combination of a native LeuC subunit including an amino acid sequence with at least 80% homology (or 90% in certain embodiments) to SEQ ID NO: 1 and a genetically modified LeuD' subunit including an amino acid sequence with at least 80% homology to SEQ ID NO: 2 and at least one modification wherein alanine, glycine, valine, or serine is independently substituted for Leu-31, His-88, or a combination thereof; a combination of a genetically modified LeuC' subunit including an amino acid sequence with at least 80% homology to SEQ ID NO: 1 and at least one modification wherein alanine, glycine, or valine is independently substituted for Val-35, Leu-411, or a combination thereof and a genetically modified LeuD' subunit including an amino acid sequence with at least 80% homology (or 90% in certain embodiments) to SEQ ID NO: 2 and at least one modification wherein alanine, glycine, valine, or serine is independently substituted for Leu-31, His-88, or a combination thereof; and/or a combination of a genetically modified LeuD' subunit including an amino acid sequence with at least 80% homology (or 90% in certain embodiments) to SEQ ID NO: 2 and at least one modification wherein alanine, glycine, valine, or serine is independently substituted for Leu-31, His-88, or a combination thereof and a native LeuD subunit including an amino acid sequence with at least 80% homology (or 90% in certain embodiments) to SEQ ID NO: 2. The genetically modified LeuCD' enzyme complexes have isopropylmalate isomerase activity.

In certain embodiments of a process for preparing a $C_7$-$C_{11}$, 2-ketoacid, the at least one modification of LeuC', (I)(C)(1)(ii), is selected from the group consisting of: (a) alanine for Val-35; (b) glycine for Val-35; (c) alanine for Val-35 and valine for Leu-411; (d) alanine for Val-35 and alanine for Leu-411; (e) alanine for Val-35 and glycine for Leu-411; and (f) glycine for Val-35 and valine for Leu-411. In other embodiments of the genetically modified LeuCD' enzyme complex, the at least one modification of the amino acid sequence of LeuD', (I)(C)(2)(ii), is selected from the group consisting of: (a) alanine for Leu-31; (b) glycine for Leu-31; (c) valine for Leu-31; (d) alanine for Leu-31 and serine for His-88; (e) glycine for Leu-31 and alanine for His-88; (f) glycine for Leu-31 and serine for His-88; and (g) valine for Leu-31 and alanine for His-88.

In some embodiments of a process for preparing a $C_7$-$C_{11}$ 2-ketoacid, the at least one genetically modified LeuCD' enzyme complex comprises a combination of (I)(C)(1)(i) and (I)(C(1)(ii), and wherein the at least one modification of the amino acid sequence of (I)(C)(2)(ii) is glycine for Leu-31. In other embodiments of a process for preparing a $C_7$-$C_{11}$ 2-ketoacid, the at least one genetically modified LeuCD' enzyme complex comprises a combination of (1) (C)(1)(ii) and (I)(C(1)(ii), wherein the at least one modification of the amino acid sequence of (I)(C)(1)(ii) is alanine for for Val-35, and wherein the at least one modification of the amino acid sequence of (I)(C)(2)(ii) is glycine for Leu-31. In some embodiments of a process for preparing a $C_7$-$C_{11}$ 2-ketoacid, the at least one genetically modified LeuCD' enzyme complex comprises a combination of (I) (C)(l)(ii) and (1)(C)(1)(ii), wherein the at least one modification of the amino acid sequence of (I)(C)(1)(ii) is alanine for Val-35 and glycine for Leu-411, and wherein the at least one modification of the amino acid sequence of (I)(C)(2)(ii) is glycine for Leu-31.

In some embodiments of a process for preparing a $C_7$-$C_{11}$ 2-ketoacid, the process further includes: (11) providing the $C_7$-$C_{11}$ 2-ketoacid with a thiamin dependent decarboxylase having thiamin dependent decarboxylase activity (e.g., a native and/or genetically modified thiamin dependent decarboxylase having thiamin dependent decarboxylase activity), under conditions the $C_7$-$C_{11}$ 2-ketoacid is converted to a $C_6$-$C_{10}$ aldehyde having one less carbon atom than the $C_7$-$C_{11}$ 2-ketoacid being converted.

In further embodiments of a process for preparing a $C_7$-$C_{11}$ 2-ketoacid, the process even further includes: (III) providing the $C_6$-$C_{10}$ aldehyde with an alcohol dehydrogenase having alcohol dehydrogenase activity (e.g., a native and/or genetically modified alcohol dehydrogenase having alcohol dehydrogenase activity), under conditions that the $C_6$-$C_{10}$ aldehyde is converted to a corresponding $C_6$-$C_{10}$ alcohol. In other embodiments, the process includes: (III) providing the $C_6$-$C_{10}$ aldehyde with an aldehyde dehydrogenase having aldehyde dehydrogenase activity (e.g., a native and/or genetically modified aldehyde dehydrogenase having aldehyde dehydrogenase activity), under conditions that the $C_6$-$C_{10}$ aldehyde is converted to a corresponding $C_6$-$C_{10}$ carboxylic acid. In certain embodiments, the process includes: (III) providing the $C_6$-$C_{10}$ aldehyde with a fatty aldehyde decarbonylase having fatty aldehyde decarbonylase activity (e.g., a native and/or genetically modified fatty aldehyde decarbonylase having fatty aldehyde decarbonylase activity), under conditions that the $C_6$-$C_{10}$ aldehyde is converted to a corresponding $C_{n-1}$ alkane.

In order to enable a non-native organism to carry out some portion of the conversions in vivo as defined hereinabove, for example, to produce the $C_6$-$C_{10}$ aldehydes and/or $C_6$-$C_{10}$ alcohols, it is desirable to perform protocols similar to that described hereunder. In general the Examples included herewith involve LeuCD enzyme engineering to alter the amino acids in order to modify enzyme functionality, particularly in terms of activity and/or specificity. This alteration in the amino acids may be used to produce modified enzymes for small scale purposes, for example, for in vitro assays, or may be the basis for genome modification in order to produce a strain of microbial organisms suitable for larger scale production.

The methodology may be carried out as is understood by those skilled in the art. In general, a suitable database, such as GenBank, is used to obtain the genetic codes for the native enzyme(s), followed by identification of the codons suitable for modification. This identification may be used as the basis for art-known methods of protein engineering, wherein computer molecular modeling identifies and also enables differentiation of structural locations at which modifications of enzyme/substrate interfaces may be effectively employed.

A given desirable modification is then performed, using a molecular biology technique called site-directed mutagenesis. The modified gene is then cloned into a replicative plasmid vector which, when transformed into a host microbial organism such as *E. coli* or *Clostridium* species, enables the production of enzymes having a higher-than-native catalytic efficiency against natural or non-natural substrates. The variant-type enzymes must be isolated from *E. coli* or *Clostridium* cells and used, either without purification or after purification, to yield an enzyme containing solution that will exhibit a higher-than-native, i.e., higher than wild type, catalytic efficiency against natural or non-natural substrates. Catalytic efficiency can be appropriately assayed in vitro, according methodologies suited to the particular enzyme. An assayed enzyme that is shown to have a desirable level of catalytic efficiency is thereby confirmed to be the product of a desirable genetic modification, and may be used for in vitro production methods. For example, such an enzyme may be used for the in vitro production of a given $C_7$-$C_{11}$ 2-ketoacid, and/or a $C_6$-$C_{10}$ aldehyde, and/or a product made from the $C_6$-$C_{10}$ aldehyde, such as a $C_6$-$C_{10}$ alcohol, carboxylic acid, or $C_5$-$C_9$ alkane.

A particular application for the above-described methodology is to produce a desirable microbial organism for large or otherwise commercial scale fermentative production of an enzyme-facilitated product, such as a $C_6$-$C_{10}$ aldehyde or one of the $C_6$-$C_{10}$ products that may be prepared therefrom. Such preparation may be carried out by inserting the DNA, or pieces of DNA, which encode for the desired improved enzyme into the genome of a second microbial organism known or believed to possess other desirable characteristics, such as, for example, capability to resist growth inhibitory effects of products during fermentation, capability to produce pyruvate (or acetyl CoA) from a particular carbon-containing substrate, or other advantageous trait(s). Thus, the second microbial organism is now genetically-modified, in that it produces a genetically modified enzyme.

In another embodiment, it is also possible to simply identify a microbial organism having native enzymes that are useful in a desired pathway, and either use that microbial organism itself as a starting microbial organism, or transfer the appropriate enzyme-encoding portion of the genome(s) of such microbial organism(s) into the genome of the organism that has been already identified as being useful for large scale fermentation production. An example of this would be to select a microbial organism that produces a suitable native thiamin dependent decarboxylase (i.e., DC) and native alcohol dehydrogenase (i.e., ADH). That microbial organism can then be used either as a starting organism or as a transformant organism to prepare a genetically modified microbial organism to produce a $C_6$-$C_{10}$ alcohol at higher yields or specificity than wild type microbial organisms.

Therefore, in some embodiments, a microbial organism including a genetically modified LeuCD' enzyme complex having isopropylmalate isomerase activity is provided. In some embodiments of a microbial organism including a genetically modified LeuCD' enzyme complex, the genetically modified LeuCD' enzyme complex includes: (a) a LeuC subunit: and (b) a LeuD subunit. The LeuC subunit (a) is selected from the group consisting of: (1) a native LeuC subunit including an amino acid sequence with at least 80% homology (or 90% in certain embodiments) to SEQ ID NO: 1; and (2) a genetically modified LeuC subunit including an amino acid sequence with at least 80% homology (or 90% in certain embodiments) to SEQ ID NO: 1 and at least one modification wherein alanine, glycine, or valine is independently substituted for Val-35, Leu-411, or a combination thereof. The LeuD subunit (b) is selected from the group consisting of: (1) a native LeuD subunit including an amino acid sequence with at least 80% homology (or 90% in certain embodiments) to SEQ ID NO: 2; and (2) a genetically modified LeuD' subunit including an amino acid sequence with at least 80% homology (or 90% in certain embodiments) to SEQ ID NO: 2 and at least one modification wherein alanine, glycine, valine, or serine is independently substituted for Leu-31. His-88, or a combination thereof. The genetically modified LeuCD' enzyme complexes are expressed in the microbial organism and have isopropylmalate isomerase activity. In certain embodiments, the microbial organism is *Escherichia coli*. In other embodiments, the microbial organism is a *Clostridium* species.

In some embodiments of a microbial organism including a genetically modified LeuCD' enzyme complex, the genetically modified LeuCD' enzyme complex includes a combination of: (a)(1) a native LeuC subunit including an amino acid sequence with at least 80% homology (or 90% in certain embodiments) to SEQ ID NO: 1: and (b)(2) a genetically modified LeuD' subunit including an amino acid sequence with at least 80% homology (or 90% in certain embodiments) to SEQ ID NO: 2 and at least one modification wherein alanine, glycine, valine, or serine is independently substituted for Leu-31, His-88, or a combination thereof. In some embodiments of a microbial organism including a genetically modified LeuCD' enzyme complex, the genetically modified LeuCD' enzyme complex includes a combination of: (a)(2) a genetically modified LeuC' subunit including an amino acid sequence with at least 80% homology (or 90% in certain embodiments) to SEQ ID NO: 1 and at least one modification wherein alanine, glycine, or valine is independently substituted for Val-35, Leu-411, or a combination thereof; and (b)(2) a genetically modified LeuD' subunit including an amino acid sequence with at least 80% homology (or 90% in certain embodiments) to SEQ ID NO: 2 and at least one modification wherein alanine, glycine, valine, or serine is independently substituted for Leu-31. His-88, or a combination thereof. In some embodiments of a microbial organism including a genetically modified LeuCD' enzyme complex, the genetically modified LeuCD' enzyme complex includes a combination of: (a)(2) genetically modified LeuC' subunit including an amino acid sequence with at least 80% homology (or 90% in certain embodiments) to SEQ ID NO: 1 and at least one modification wherein alanine, glycine, or valine is independently substituted for Val-35, Leu-411, or a combination thereof; and (b)(1) a native LeuD subunit including an amino acid sequence with at least 80% homology (or 90% in certain embodiments) to SEQ ID NO: 2.

In certain embodiments of a microbial organism including a genetically modified LeuCD' enzyme complex, at least one modification of LeuC' is selected from the group consisting of: (a) alanine for Val-35; (b) glycine for Val-35; (c) alanine for Val-35 and valine for Leu-411; (d) alanine for Val-35 and alanine for Leu-411; (e) alanine for Val-35 and glycine for Leu-411; and (f) glycine for Val-35 and valine for Leu-411. In other embodiments a microbial organism including a genetically modified LeuCD' enzyme complex, the at least one modification of the amino acid sequence of LeuD', is selected from the group consisting of: (a) alanine for Leu-31; (b) glycine for Leu-31; (c) valine for Leu-31; (d) alanine for Leu-31 and serine for His-88; (e) glycine for Leu-31 and alanine for His-88; (f) glycine for Leu-31 and serine for His-88; and (g) valine for Leu-31 and alanine for His-88.

In some embodiments of a microbial organism including a genetically modified LeuCD' enzyme complex, the genetically modified LeuCD' enzyme complex comprises a combination of (a)(1) and (b)(2), wherein the at least one modification of the amino acid sequence of (b)(2) is glycine for Leu-31. In some embodiments of a microbial organism including a genetically modified LeuCD' enzyme complex, the genetically modified LeuCD' enzyme complex comprises a combination of (a)(2) and (b)(2), wherein the at least one modification of the amino acid sequence of (a)(2) is alanine for for Val-35, and wherein the at least one modification of the amino acid sequence of (b)(2 is glycine for Leu-31. In some embodiments of a microbial organism including a genetically modified LeuCD' enzyme complex, the genetically modified LeuCD' enzyme complex comprises a combination of (a)(2) and (b)(2), wherein the at least one modification of the amino acid sequence of (a)(2) is alanine for Val-35 and glycine for Leu-411, and wherein the at least one modification of the amino acid sequence of (b)(2) is glycine for Leu-31

EXAMPLES

Example 1: Preparing the Genetically Modified LeuCD' Enzyme Complexes Having Increased Activity Against 2-Hexylmalate (2-HM)

During 2-ketononanoate biosynthesis by the recursive activity of the LeuABCD pathway, 2-alkylmalic acids of varying lengths are formed as substrates of LeuCD. For efficient biosynthesis of 2-ketononanoate, it is desired that LeuCD efficiently capture 2-ethylmalate (intermediate II, n=1; FIG. 1), 2-propylmalate (2-IPM; Intermediate II, n=2; FIG. 1), 2-butylmalate (Intermediate II, n=3; FIG. 1), 2-pentylmalate (Intermediate II, n=4; FIG. 1) and 2-hexylmalate (2-HM; Intermediate II, n=5; FIG. 1) for catalysis. The native LeuCD is relatively inefficient in capturing longer nonnatural 2-alkylmalate substrates. To improve the efficiency of native LeuCD in capturing 2-hexylmalate for catalysis, the active site of native LeuCD enzyme complex was modified using protein engineering techniques as described hereinbelow.

E. coli isopropylmalate isomerase (LeuCD) is a heterodimer made up of a 50 kDa subunit called LeuC and a 22.4 kDa subunit called LeuD. Both the subunits, come together to form a functional enzyme having the active site at the dimer interface. Residues lining the 2-isopropylmalate binding site of E. coli LeuCD were identified from a structural model of LeuCD that is constructed via homology modeling and using as the template the crystal structure model of pig aconitase (Protein Data Bank (PDB) code 1 ACO) and isopropylmalate isomerase small unit of Campylobacter jejuni (PDB ID code 3Q3W) (FIG. 2). Initially, models of the LeuC and LeuD subunits were constructed separately using the molecular modeling program MOE (Chemical Computing Group Inc. Montreal Canada), and the pig aconitase (PDB code 1ACO) and the small subunit of Campylobacter jejuni (PDB ID code 3Q3W) as templates, respectively. The functional complex was generated by overlaying both the subunit models on the two domains of aconitase. The 4Fe-4S cluster and the transaconitase present in the active site of pig aconitase crystal structure model were used as templates to build a kinetically competent model of LeuCD with substrates, 2-isopropylmalate and 2-hexylmalate, bound within the active site. Residues Val-35 and Leu-411 in LeuC and Leu-31, and His-88 in LeuD were found to be near the isopropyl and hexyl group of the substrates, and were selected for modification (FIG. 2). Each of these residues was modified to an amino acid residue with smaller hydrophobic side chain to make room for the bulkier alkyl group. As shown in Table 1, 15 variants were designed for evaluation.

TABLE 1

LeuCD variants generated by coexpressing various LeuC and LeuD subunits and activity of LeuCD variants.

| Variant No. | LeuC subunit | LeuD subunit | Activity, pmol · min⁻¹ · ug⁻¹ | | |
|---|---|---|---|---|---|
| | | | 2-IPM | 2-BM | 2-HM |
| 3 | Wt LeuC | Wt LeuD | 368 ± 6.2 | 1247 ± 1 | 0.63 ± 0.01 |
| 1 | V35A | Wt LeuD | 1.3 ± 0.0 | 52 ± 1 | 40 ± 0.8 |
| 5 | Wt LeuC | L31A | 1.7 ± 0.0 | 245 ± 4 | 6.2 ± 0.2 |
| 6 | Wt LeuC | L31G | 0.0 ± 0.0 | 30 ± 1 | 215 ± 6.4 |
| 9 | V35A | L31G | 0.0 ± 0.0 | 1.7 ± 0.0 | 51 ± 1.4 |
| 10 | V35G | L31V | 0.7 ± 0.0 | 11 ± 0.3 | 2.4 ± 0.1 |
| 18 | L411V | L31G | 0.0 ± 0.0 | 1.3 ± 0.0 | 12 ± 0.0 |
| 31 | V35A/L411V | L31V | 4.7 ± 0.3 | 54 ± 1.2 | 2.8 ± 0.1 |
| 32 | V35A/L411V | L31A | 0.0 ± 0.0 | 4.7 ± 0.1 | 3.1 ± 0.2 |
| 35 | V35A/L411A | L31A | 0.0 ± 0.0 | 0.6 ± 0.0 | 0.4 ± 0.00 |
| 36 | V35A/L411A | L31G | 0.0 ± 0.0 | 0.0 ± 0.0 | 0.84 ± 0.01 |
| 38 | V35A/L411G | L31A | 0.0 ± 0.0 | 1.0 ± 0.0 | 0.6 ± 0.01 |
| 39 | V35A/L411G | L31G | 0.0 ± 0.0 | 0.0 ± 0.0 | 3.1 ± 0.0 |
| 59 | Wt LeuC | L31V/H88A | 1.2 ± 0.0 | 33 ± 1.0 | 27.4 ± 0.2 |
| 61 | Wt LeuC | L31G/H88A | 0.0 ± 0.0 | 1.2 ± 0.0 | 11.6 ± 0.2 |
| 64 | Wt LeuC | L31G/H88S | 0.0 ± 0.0 | 0.8 ± 0.0 | 7.5 ± 0.1 |
| 115 | V35G/L411V | L31A/H88S | 0.0 ± 0.0 | 0.0 ± 0.0 | 1.4 ± 0.02 |

*LeuC and LeuD subunits are identified by the modifications made to the wild type amino acid sequence. The notation for these specific genetic modifications, as well as similar notations for genetic modifications disclosed throughout the instant specification, adhere to industry standard wherein amino acid modifications are defined as the original single letter amino acid code, followed by the amino acid position, followed by the new amino acid single letter code. L = leucine; A = alanine; G = glycine; V = valine; S = serine; and I = isoleucine.

Each of the engineered LeuCD variants is expressed, isolated, and then evaluated without further purification for activity against 2-isopropylmalate (i.e., 2-IPM), 2-butylmalate (i.e. 2-BM) and 2-hexylmalate (i.e., 2-HM), as described below, 2-IPM is the natural substrate of LeuCD and is formed in the microbial organisms during the biosynthesis of leucine, 2-BM and 2-HM are non-natural substrates of LeuCD that would be formed inside the cells during $C_7$-$C_{11}$ 2-ketoacid, for example, 2-ketononanoate, biosynthesis.

The evaluation of the LeuCD' variants was performed in two steps using the enzyme assay described below. The variants were initially tested for activity against a single high concentration of 2-IPM, 2-BM and 2-HIM. The assay involved coupling the LeuCD reaction with that of the LeuB reaction. Thus, during the assay, 2-IPM was initially isomerized to 3-isopropylmalate (3-IPM) by LeuCD which was immediately converted to 4-methyl-2-ketovalerate by the LeuB enzyme present in the assay mixture. Likewise, in the assays involving 2-BM or 2-HM as substrates, the end product formed in the assay was 2-ketoheptanoate or 2-ketononanoate, respectively. The activity of LeuCD variant was calculated from the amounts of respective 2-ketoacids produced in the coupled assay. LeuCD' variants that have higher activity than the wild type enzyme in converting all or some of the 2-alkylmalate substrates, such as 2-HM, to the corresponding $C_7$-$C_{11}$ 2-ketoacid, are desirable because they improve the overall efficiency and avoid bottlenecking of the relevant "+1" LeuABCD pathway of FIG. 1. Following the initial evaluation, a more detailed kinetic analysis is performed on a select number of LeuCD variants to determine the maximal rate (i.e., $k_{cat}$), Michaelis-Menten constant (i.e., $K_M$), and the catalytic efficiency of the enzyme (i.e., $k_{cat}/K_M$) for some of the substrates.

Example 2: Expression of LeuCD Variants in E. coli

To evaluate the substrate specificity of the wild type LeuCD and the engineered LeuCD' variants listed in Table 1, genes of each complex were expressed into E. coli cells separately. The gene sequences of LeuC (EcoGene Accession No. EG 11576 (Sequence Listing, SEQ ID 1) and LeuD (EcoGene Accession No. EG 11575) were downloaded from the E. coli genome website. EcoGene (ecogene.org). Codons of 13 additional amino acids that included six histidines were fused upstream of the codon of Met-1 of LeuC gene sequence. Such a modification allowed expression of a His-tagged LeuC having 13 additional amino acids on the N-terminus. To the resulting modified gene, additional bases were added to introduce a NcoI and a SacI restriction site at the 5'- and 3'-end, respectively, for cloning purposes. The whole DNA sequence was chemically synthesized and cloned into an *E. coli* expression vector, pRSFDuet-1 (purchased from EMD Biosciences) at the NcoI and SacI sites by SGI Inc. To the downloaded LeuD gene sequences, additional bases were added to introduce a NdeI and XhoI restriction sites at the 5'- and 3'-end, respectively. The resulting modified gene was also chemically synthesized and cloned into an *E. coli* expression vector, pETDuet-1 vector, at the NdeI and XhoI restriction sites by SGI Inc. The genes of the additional LeuC and LeuD variants were also chemically synthesized and cloned into the pRSFDuet and pET-Duet vectors, respectively Fully functional isopropylmalate isomerase (i.e., LeuCD) was produced in *E. coli* BL21(DE3) (purchased from EMD Biosciences) cells by cotransfecting them with individual LeuC and LeuD subunit expressing vectors. Different LeuCD variants were produced by cotransfecting different combinations of LeuC and LeuD variant vectors in *E. coli* cells. Table 1 shows the LeuC and LeuD vector combination that was used for producing corresponding LeuCD variant in *E. coli*. It is noted that none of the Sequence Listings included herein show the histidine-tag that is used, which in this case is Gly-Ser-Ser-His-His-His-His-His-His-Ser-Ser.

Cotransfection of the *E. coli* BL21(DE3) cells with the LeuC and LeuD expression vectors was performed using standard procedures. Cells harboring the expression vectors were selected on LB agar plates containing 100 μg/mL of ampicillin and 50 μg/mL of kanamycin. A starter culture was started by transferring a single colony of transformant into 50 mL of LB medium containing 100 μg/mL of ampicillin and 50 μg/mL of kanamycin and incubated at 37° C. with shaking at 220 rpm overnight. On the next day, 7 mL of starter culture was inoculated into 800 mL of Terrific Broth (TB) and the culture was incubated at 37° C. until it reached an $OD_{600\ nm}$ of 0.5. Isopropyl β-D-1-thiogalacto-pyranoside (IPTG) at a final concentration of 1 mM was added to induce the expression of the LeuCD complex or its variant and the culture was transferred to a 15° C. incubator for 16 hours (h). At the end of 16 h, the culture was centrifuged at 8000 revolutions per minute (rpm) to pelletize the cells. The cell pellet was divided into four aliquots and stored at −80° C. until disruption for the isolation of the LeuCD complex.

The LeuCD complex was isolated from the cell pellet in an anaerobic chamber (acquired from COY Lab Products (MI, USA)) maintained under 98% nitrogen and 2% Hydrogen. The *E. coli* pellet prepared in [0055] was suspended in 50 mM HEPES buffer (pH 8.0) containing 0.2 mM ferrous ammonium sulfate, 10 mM DTT, 30 mM KCl, 5 mM $MgCl_2$ and protease inhibitor cocktail (acquired from SIGMA-ALDRICH, USA). To the cells, 2.5 gm of 0.1 mm glass beads were added and the cells were disrupted on a Geno grinder for 3 minutes at 1750 rpm. Cell debris and the glass beads were pelleted by centrifugation and the supernatant was mixed with equal volume of 50% glycerol and stored anaerobically at −20° C.

Functional evaluation of each LeuCD variant was performed using the whole cell lysate from the cells in which it was produced. For comparing the catalytic efficiencies of each LeuCD complex, the amounts of LeuC and LeuD variant in the whole cell lysate was determined using microfluidic capillary electrophoresis on Labchip GX II (Perkin Elmer Inc. Waltham, Mass.) equipped with a fluorescent detector. Cell lysates were prepared for capillary electrophoresis using the manufacturer supplied reagents and protocol. Briefly, 4 μL aliquots of the cell extract was mixed with 14 μL of denaturing buffer. The mixture was heated at 100° C. for 5 minutes and were allowed to cool to room temperature. After cooling, 70 μL sterile water was added to the mixture and was analyzed using the protocol supplied by PerkinElmer. LabChip GX II software analyzed and reported the size, relative concentration and purity of the LeuC and LeuD detected in each sample. Cell extracts from cells containing empty vectors served as a negative control for identification of LeuC and LeuD proteins in the extracts. Analytical grade Bovine Serum Albumin (BSA) standard solution (2 mg/mL) supplied by Pierce Biotechnology (Rockford, Ill.) was used as standard for quantification. In all the LeuCD complex containing extracts. LeuC subunit was the limiting subunit. The activity of each LeuCD extract was normalized with respect to the amount of LeuC present in the extract.

Example 3: Determination of the Substrate Specificity of the Wild Type and the Engineered LeuCD' Variants A high-throughput LeuCD enzyme assay was developed for the screening and kinetic evaluation of LeuCD' variants, as prepared in Examples 1 and 2, for activity against 2-isopropylmalate (i.e., 2-IPM), 2-butylmalate (2-BM) and 2-hexylmalate (i.e., 2-H1M). The coupled assay involved coupling the LeuCD reaction with that of the LeuB reaction. Thus, during the assay, 2-IPM was initially isomerized to 3-isopropylmalate (3-IPM) by LeuCD which was immediately converted to 4-methyl-2-ketovalerate by the LeuB enzyme present in the assay mixture. Likewise, in the assays involving 2-BM or 2-H1M as substrates, the end product formed in the assay was 2-ketoheptanoate or 2-ketononanoate, respectively. The activity of LeuCD variant was calculated from the amounts of respective 2-ketoacids produced in the coupled assay.

The HTP LeuCD coupled assay used for screening the activity of each variant involved incubating the whole cell lysate from cells expressing the LeuCD variant with 2.6 mM 2-isopropylmalate (i.e., 2-IPM), 2-butylmalate (i.e., 2-BM) or 2-hexylmalate (i.e., 2-HM), in a mixture containing: 20 μg of wild type LeuB, 16 μg of a L96G/V198A variant of LeuB, 5 mM $NAD^+$, 10 mM DTT, 20 μg bovine serum albumin. 30 mM KCl, 5 mM $MgCl_2$, and 50 mM HEPES pH 8. The total assay volume was 100 μL and was performed anaerobically in a COY chamber at room temperature for a period of 1 hr. The reaction was stopped by the addition of an equal volume of a mixture containing 20% formic acid and 10% methanol. The 2-ketoacids formed in the coupled assay were quantitated using an Agilent 1290 Infinity uHPLC coupled with an AB Sciex 5500 QTrap mass spectrometer. Following the separation of the 2-ketoacids on Waters Acquity HISS T3 1.8 μM 3.0×150 mm reverse phase column under reverse phase conditions, the detection and quantitation was performed in the mass spectrometer by single quadrupole select ion monitoring method that operated in negative mode. Quantitation was based off an external calibration curve generated for each 2-ketoacid from custom synthesized analytical grade standard reference material with the exception of 4-methyl-2oxovalerate which was commercially available from Sigma-Aldrich.

The activities were normalized with the amounts of LeuC subunit in the whole cell lysate, 2-IPM is the native substrate of LeuCD and activity against it would indicate that the engineered enzymes would be able to catalyze the earlier cycles of "+1" pathway during 2-ketobutyrate elongation to 2-KN, 2-BM and 2-HM are the non-native substrates of LeuCD. LeuCD variants having higher activity against 2-HM than the wild type LeuCD would be capable of improving octanol yield by making the later cycles of "+1" pathway during 2-KN formation more efficient. The HTP assay involved coupling of the LeuCD activity with that of the next enzyme in the "+1" LeuABCD pathway, isopropylmalate dehydrogenase (i.e., LeuB). Thus, 3-isopropylmalate (i.e., 3-IPM), 3-butylmalate or 3-hexylmalate (i.e., 3-HM) produced from 2-IPM, 2-BM or 2-HM, respectively, by LeuCD were oxidatively decarboxylated by LeuB to 2-ketoisocaproate, 2-ketoheptanoate and 2-ketononanoate (i.e., 2-KN). All the three 2-ketoacids were then quantitated using LC/MS.

As shown in Table 1, the wild type LeuCD (Variant 3) is highly active against 2-IPM and 2-BM, while having very little activity against 2-HM. Table 1 also highlights that 13 LeuCD variants had 2-340 fold higher activity than the wild type LeuCD in isomerizing 2-hexylmalate to 3-hexylmalate. Residue Val-35 within the LeuC subunit and Leu-31 within LeuD had a major impact on improving the activity against 2-HM. For example, Variants 1 (i.e., V35A-LeuC+wt LeuD) and 6 (i.e., wt LeuC+L31G-LeuD), respectively had 63- and 341-fold higher activity against 2-H1M than the wild type LeuCD (i.e., Variant 3). While the V35A and L31G substitutions in LeuC and LeuD, respectively increased the activity against 2-HM, they significantly diminished activity against 2-IPM. Together, the data indicate that Variants 1 and 6 would be significantly less effective than the wild-type enzyme in the earlier cycles of "+1" pathway during the elongation of 2-ketobutyrate, but will be 60 to 350 fold more efficient during later stages of elongation of 2-ketobutyrate to 2-ketononanoate. Expressing both the wild type LeuCD and variant 1 or 6 would improve the elongation of 2-ketobutyrate to $C_7$-$C_{11}$ 2-ketoacids and eventually. $C_6$-$C_{10}$ alcohols.

Example 4: Determination of the Catalytic Efficiencies of the LeuCD Variants Showing High Specificity for 2-Hexylmalate (2-HM)

Following the initial evaluation, a more detailed kinetic analysis was performed on the wild type LeuCD and a select number of variants to determine the maximal rate (i.e., $k_{cat}$), Michaelis-Menten constant (i.e., $K_M$), and the catalytic efficiency of the enzyme (i.e., $k_{cat}/K_M$) for 2-IPM, 2-BM and 2-HM. The kinetic determinations were performed using the HTP enzyme assay described above, with minor modifications. During the kinetic parameter determinations, 2-IPM, 2-BM, and 2-HM concentrations were varied from 0-0.625 mM, 0-5 mM, and 0-1.6 mM, respectively. The assay was carried out for 30 min and the amount of wild type or LeuCD variant extract was adjusted to limit substrate consumption below 20%. For the maximal rate ($k_{cat}$) calculations, the amount of LeuCD complex present in the enzyme reaction was determined on the basis of the amount of LeuC determined using the microfluidic capillary electrophoresis on Labchip GX II (Perkin Elmer Inc, Waltham, Mass.). The kinetic parameters were calculated by fitting the activity in the assay to Michaelis-Menton equation using the Graphpad Prizm software.

TABLE 2

Kinetic parameters of LeuCD complexes.

| | 2-IPM | | | 2-BM | | | 2-HM | | |
|---|---|---|---|---|---|---|---|---|---|
| Variant | $k_{cat}$, hr$^{-1}$ | $K_M$, mM | $k_{cat}/K_M$, mM$^{-1}$ hr$^{-1}$ | $k_{cat}$, hr$^{-1}$ | $K_M$, mM | $k_{cat}/K_M$, mM$^{-1}$ hr$^{-1}$ | $k_{cat}$, hr$^{-1}$ | $K_M$, mM | $k_{cat}/K_M$, mM$^{-1}$ hr$^{-1}$ |
| 3 | 1526 ± 58 | 0.068 ± 0.01 | 22366 ± 2375 | 6120 ± 323 | 1.33 ± 0.14 | 4646 ± 554 | | | 4 ± 1 |
| 1 | | | | 542 ± 83 | 3.9 ± 0.7 | 145 ± 34 | 314 ± 55 | 3.35 ± 0.75 | 98 ± 28 |
| 5 | | | | 1400 ± 77 | 1.31 ± 0.14 | 1077 ± 129 | 35 ± 5 | 1.4 ± 0.6 | 29 ± 13 |
| 6 | | | | 477 ± 120 | 8.44 ± 2.4 | 62 ± 24 | 1237 ± 34 | 0.65 ± 0.04 | 1917 ± 129 |
| 9 | | | | | | 2 ± 0.0 | 166 ± 5 | 0.6 ± 0.034 | 283 ± 18 |
| 59 | | | | 218 ± 22 | 2.7 ± 0.4 | 83 ± 14 | 182 ± 37 | 3.8 ± 0.9 | 50 ± 16 |
| 61 | | | | | | 1.0 ± 0.0 | | | 22 ± 2 |

As highlighted in Table 2, the wild type LeuCD complex (Variant 3) is highly efficient in catalyzing its natural substrate, 2-IPM. The wild type enzyme preferred its non-natural substrates, 2-BM and 2-HM, less as evident by their lower $k_{cat}/K_M$ values, 2-HM was the least preferred substrate. All the LeuCD variants, Variants 1, 5, 6, 9, 59 and 61 showed 5-480 fold improvement in catalytic efficiency for 2-TIM over the wild type enzyme. The kinetic data also show that variant 5 was more efficient ($k_{cat}/K_M$) at catalyzing isomerization of 2-BM than that of 2-HM while variants 6, 9 and 61 were more efficient in catalyzing 2-HM over 2-BM. Variants 1 and 59 showed very similar efficiencies in catalyzing the isomerizations of 2-BM and 2-HM.

Example 5: In Vivo Production of $C_4$-$C_8$ Alcohols in Engineered Strains of E. coli Using Wild Type LeuCD and its Variants in Combination with the '+1 Pathway' Enzymes Strain Construction The effects of LeuCD variants on alcohol production was evaluated in an engineered MG1655 strain of *Escherichia coli* (*E. coli*). The MG1655 strain was modified to improve linear alcohol production, enable expression of the genes from the Plac promoters and impart clonal stability. Improvements for linear alcohol production involved knocking down of the ilvBN and ilvIH genes, and upregulation of the ilvA gene in *E. coli* MG1655. Knock-out of ilvBN and ilvIH genes eliminated branched chain alcohol production, while upregulation of the ilvA gene increased the production of 2-ketobutyrate. Upregulation of ilvA was effected by replacing its native promoter and ribosome binding site with a strong constitutive promoter, BBa_J23119 and a synthetic ribosome binding site, BBa_B0034. Both the strong constitutive promoter and the synthetic ribosome binding site were obtained from the Registry of Standard Biological Parts (parts.igem.org), a database of biological parts curated by iGEM (International Genetically Engineered Machine Competition). The knocking out of the ilvBN and ilvIH genes and the replacement of the native promoter and ribosome binding site of ilvA gene was performed via lambda(red)-mediated recombination as described by Datsenko and Wanner (PNAS 97(12):6640-6645). To enable expression of the genes from the Plac promoters, the DE3 lysogen was integrated into MG1655 using the λDE3 Lysogenization Kit (EMD Millipore Cat #69734). To ensure clonal stability, recA was inactivated by λRed-mediated homologous recombination. The genotype of the resulting strain that was used for the alcohol production studies was MG1655(DE3) ΔrecA ΔilvBN ΔilvIH ilvAup.

Vector Construction

During the evaluation of the effects of LeuCD variants on $C_4$-$C_8$ alcohol production in the engineered MG1655 E. coli strain, the following seven enzymes were coexpressed: i) Native E. coli isopropylmalate synthase (LeuA; GenBank: Accession No. NC_000913.3 Gene ID: 947465), ii) LeuA* (H97A/S139G/N167G/P169A/G462D variant of E. coli IPMS described by Marcheschi et al ACS Chem. Biol. 2012, 7, 689-697), iii) native E. coli isopropylmalate isomerase (LeuCD; GenBank:Accession No. NC_000913.3 Gene ID: 94576 and Gene ID: 945642), iv) isopropylmalate isomerase variants described in Table 3, v) E. coli isopropylmalate dehydrogenase (LeuB; GenBank:Accession NO. NC_000913.3 Gene ID: 944798), vi) F381L/V461A variant of ketoisovalerate decarboxylase (KIVD*) from Lactocossus lactis (described by Zhang et. al PNAS, 2008, 105, 20653-20658), and vii) S. cerevisiae alcohol dehydrogenase (ADH6; GenBank: Accession No. NC_001145.3 GeneID: 855368). All the enzymes were expressed in E. coli using the two expression vectors, pZE_LeuABCD-KA6 and pZAlac_ilvAleuA described by Marcheschi et al (ACS Chem. Biol. 2012, 7, 689-697). pZE_LeuABCD-KA6 was acquired from Dr. Liao's group and used without any further modification. pZE_LeuABCD-KA6 expressed LeuA* (H97A/S139G/N167G/P169A/G462D variant of E. coli IPMS described by Marcheschi et al ACS Chem. Biol. 2012, 7, 689-697), LeuB. LeuC. LeuD, and KiVD* (F381 L/V461A variant of ketoisovalerate decarboxylase from Lactocossus lactis described by Zhang et. al PNAS, 2008, 105, 20653-20658) in the engineered MG1655 strain. Vector pZAlac_ilvAleuA, that had a copy of Ilva and wild type LeuA genes, was modified to express the LeuCD variant genes described here. Eleven vectors containing the LeuC and LeuD variant genes as shown in Table 3 were constructed for the evaluation of the effects on alcohol composition in the engineered MG1655 strain. FIG. 7 shows a typical modified vector, pOC-CL-0 ###, that was used along with pZE_LeuABCD-KA6 for the alcohol production studies. As shown in FIG. 7 and listed in Table 3, each pOC-CL-0 ###vector had a LeuC* and LeuD* gene that expressed a given LeuCD variant, a native E. coli isopropylmalate isomerase, and the ilvA gene protein. All the genes in both the vectors were under pLacO1 promoter and induced using Isopropyl β-D-1-thiogalactopyranoside (IPTG).

The genes of LeuC and LeuD variants were cloned into the pZAlac_ilvAleuA vector in two steps using the Gibson assembly technology of New England Bioscience. The first step involved insertion of the LeuD variant gene as a cassette (shown in FIG. 8A) at the ZraI site of the pZAlac_ilvAleuA vector. The LeuD variant gene cassette was generated as a Gblock (by Integrated DNA Technologies) and had a placO1 promoter, ribosome binding site (rbs), and a unique NheI site on the 5' side of the LeuD variant gene (FIG. 8A). A terminator sequence and unique restriction sites were placed on the 3'-end of the LeuD variant gene (FIG. 8A). The second step in the vector construction involved introduction of the LeuC variant gene as a PCR generated cassette (FIG. 8B) using the Gibson assembly technology. The arrangement of genes in the final resulting vector as identified by the pOC-CL-0 ###vector is shown in FIG. 2. For alcohol production, the engineered MG1655 strain of E. coli (MG1655(DE3) ΔrecA ΔilvBN ΔilvIH ilvAup) was transformed with the pZE_LeuABCD-KA6 vector (FIG. 6) containing the full pathway and one of the pOC-CL-0 ###vector listed in Table 3.

TABLE 3

Vectors containing the LeuC and LeuD variant genes constructed for the evaluation of the effects on alcohol composition in the engineered MG1655 strain.

| Variant | LeuC | LeuD | pOC-CL-0### |
| --- | --- | --- | --- |
| 1 | V35A | Wt LeuD | pOC-CL-0122 |
| 2 | V35G | Wt LeuD | pOC-CL-0123 |
| 3 | Wt LeuC | Wt LeuD | pOC-CL-0124 |
| 6 | Wt LeuC | L31G | pOC-CL-0112 |
| 9 | V35A | L31G | pOC-CL-0113 |
| 10 | V35G | L31V | pOC-CL-0127 |
| 38 | V35A/L411G | L31A | pOC-CL-0129 |
| 39 | V35A/L411G | L31G | pOC-CL-0114 |
| 59 | Wt LeuC | L31V/H88A | pOC-CL-0115 |
| 61 | Wt LeuC | L31G/H88A | pOC-CL-0128 |
| 115 | V35G/L411V | L31A/H88S | pOC-CL-0130 |

Alcohol Production in Engineered MG1655 Cells

MG1655 strains transformed with the pZE_LeuABCD-KA6 and one of the pOC-CL-0 ###vectors listed in Table 3 were selected on LB agar plates containing 100 ug/mL ampicillin and 25 ug/mL kanamycin. A 50 mL starter culture in LB medium containing 100 ug/mL ampicillin and 25 ug/mL kanamycin was initiated using a single colony from the dual antibiotic LB agar plate and incubated overnight at 37° C. in an incubator shaker set at 200 rpm. After 12-16 hours of incubation, serum bottles containing 5 mL of sterile modified 2×M9 medium (composition shown in Table 4) with 100 ug/mL ampicillin and 25 ug/ml kanamycin were inoculated with 50 uL of starter culture.

TABLE 4

Medium composition used to demonstrate alcohol production from E. coli recombinantly engineered to contain the '+1 pathway' in combination with LeuCD variants.
2X M9 Medium

| | Conc (g/L) |
| --- | --- |
| NA2HPO4 | 13.56 |
| KH2PO4 | 6 |
| NH4Cl | 2 |
| NaCl | 1 |
| Yeast Extract | 10 |
| Glucose | 40 |
| 92949 Trace Metal Mix A5 w/ Co | 1 |

Cultures were incubated at 37° C. with shaking at 200 rpm and induced after 3 hrs using 0.1 mM of IPTG to express all the genes. The culture temperature was reduced to 30° C. after induction. Cultures were harvested 44 hours after induction by transferring them to 4° C. for 20-30 minutes. Serum bottles were then de-capped, and 1 mL of the fermentation broth was quickly poured into a 15 mL conical tube containing 1 mL of a saturated sodium chloride solution and 2 mL of analytical grade toluene. The broth-sodium chloride-toluene mixture was vortexed for 30 seconds and the toluene extract was subjected to alcohol analysis using a GC/FID method described in WO2016094604 A1, which is incorporated herein by reference in its entirety.

Table 5 shows the effects of 10 LeuCD variants on the alcohol composition in the strains expressing them along with the other genes mentioned above. Several of the LeuCD variant expressing cells produced higher amounts of heptanol and/or octanol than the strain expressing only the wild type LeuCD. This suggests that the LeuCD variants reported here are overcoming the barrier towards the production of >$C_7$ alcohols using the non-natural pathway described here. ANOVA analysis of the data shows that LeuCD variants 6 and 59 increased heptanol titers (FIG. 9A), while variants 6, 9, 10, 38, 39, and 61 increased octanol titers (FIG. 9B) that were significantly higher than those produced by the wild type enzyme. Cells expressing LeuCD variants 6, 9 or 39 produced >6-fold higher amounts of octanol than the WT LeuCD enzyme (FIG. 9B).

the efficiency of the wild type LeuCD complex decreases as the size of the alkyl chain increases, with 2-HM being a poor substrate. Under these conditions, addition of Variant 6 to the reaction mixture would improve the efficiency of the pathway in producing 2-ketononanoate.

For the optimal efficiency of the "+1" iterative pathway, for making 2-ketononanoate in vivo the LeuCD complex combination needs to match its efficiency in catalyzing the conversion of each intermediate 2-alkylmalate with the efficiency of other enzymes within the cell and also other competing metabolic pathways within the cell. Under such circumstances, any of the variants listed in Table 1 (or Table 5) may be suited better even though they may not be having the highest efficiency in isomerizing 2-HM.

The LeuCD' variants were initially screened for activity against a single high concentration of 3-IPM, 2-BM and 3-HM before determining the catalytic efficiency of selected few (Tables 1 and 2). Without wishing to be bound by any theory, the results illustrated in Table 2 may be interpreted as suggesting that replacing Val-35 and/or Leu-411 of LeuC with amino acids having smaller hydrophobic side chains, e.g., valine, alanine for Val-35 and/or valine, alanine, or glycine for Leu-411, and/or Leu-31 and/or His-88 of LeuD with amino acids having smaller hydrophobic side chains, e.g., valine, alanine, or glycine for Leu-31 and/or serine or alanine for His-88, may in some instances simultaneously decrease enzyme activity against 3-IPM, and increase enzyme activity against 3-HM. As shown in Table 1, various

TABLE 5

The mean alcohol titers for serum bottle fermentations of E. coli containing the '+1 pathway' enzymes in combination with the WT and variant LeuCD enzymes.

| Variant # | 1-Butanol | 1-Pentanol | 1-Hexanol | 1-Heptanol | 1-Octanol | Total Alcohols |
|---|---|---|---|---|---|---|
| WT | 238.5 ± 12.0 | 139.1 ± 4.8 | 69.2 ± 1.1 | 83.9 ± 1.2 | 2.3 ± 0.2 | 533.1 ± 18.9 |
| 1 | 242.4 ± 8.1 | 145.0 ± 7.2 | 72.4 ± 4.4 | 87.0 ± 5.4 | 2.4 ± 0.2 | 549.2 ± 25.3 |
| 2 | 242.1 ± 8.5 | 144.9 ± 3.4 | 72.9 ± 1.2 | 87.5 ± 2.0 | 2.4 ± 0.3 | 549.8 ± 14.1 |
| 115 | 248.6 ± 12.0 | 144.0 ± 8.6 | 71.9 ± 3.6 | 82.8 ± 4.3 | 2.6 ± 0.1 | 550.0 ± 28.6 |
| 61 | 252.7 ± 9.8 | 146.1 ± 6.5 | 73.5 ± 3.7 | 85.9 ± 6.5 | 3.9 ± 0.5 | 562.2 ± 26.8 |
| 10 | 257.9 ± 7.6 | 125.6 ± 1.2 | 58.8 ± 0.7 | 80.3 ± 1.3 | 4.1 ± 0.6 | 526.7 ± 9.8 |
| 38 | 275.0 ± 17.2 | 142.7 ± 5.1 | 74.7 ± 1.6 | 79.8 ± 3.8 | 5.6 ± 0.7 | 577.8 ± 27.9 |
| 59 | 302.2 ± 9.4 | 159.2 ± 5.0 | 66.8 ± 2.5 | 95.5 ± 3.9 | 6.8 ± 0.4 | 630.6 ± 17.3 |
| 6 | 289.4 ± 6.0 | 160.3 ± 6.0 | 72.4 ± 3.7 | 93.9 ± 4.7 | 14.2 ± 0.4 | 630.2 ± 19.6 |
| 9 | 310.2 ± 12.6 | 158.8 ± 7.9 | 65.5 ± 4.9 | 84.8 ± 8.7 | 15.0 ± 0.8 | 634.4 ± 34.3 |
| 39 | 292.6 ± 16.2 | 145.9 ± 10.2 | 63.0 ± 7.1 | 76.0 ± 9.2 | 18.2 ± 1.2 | 595.7 ± 42.9 |

* ADH6 and kivD were also included in all strain constructs. All titers are shown in milligrams per liter ± standard deviation across a minimum of triplicate experiments. Titers were measured 44 hours after induction.

Example 6: Results and Discussion

To improve the efficiency of the "+1" pathway in producing 2-ketononanoate, isopropylmalate isomerase would desirably efficiently catalyze isomerization of all the intermediate 2-alkylmalates to their corresponding 3-alkylmalates. The three substrates used for the evaluation of LeuCD variants are representative of these intermediate 2-alkylmalates. More specifically, 2-isopropylmalate (i.e., 2-IPM) is representative of the shorter 2-alkylmalate substrates expected to form during the earlier cycles of the "+1" iterative pathway; 2-butylmalate (i.e., 2-BM) and 2-hexyl-malate (i.e., 2-HIM) are mid to largest 2-alkylmalates, respectively, formed in the iterative pathway en route to 2-ketononanoate formation. For the optimal efficiency of the "+1" iterative pathway for synthesizing 2-ketononanoate in vitro, the LeuCD complex combination needs to efficiently catalyze the conversion of each intermediate 2-alkylmalate to its corresponding 3-alkylmalate. As evident from Table 2, combinations of these variants exhibited higher activity than the wild type enzyme against 3-HM. This analysis suggests that the wild type LeuCD is highly efficient in capturing its native substrate, i.e., 2-IPM, for catalysis, but becomes a progressively less active as a catalyst as the "+1" pathway iterates for elongating 2-ketobutyrate to a $C_7$-$C_{11}$ 2-ketoacid, such as, in this instance, 2-ketononanoate. Variants 1 (V35A-LeuC+wt LeuD), 5 (wt-LeuC+L31A LeuD), 6 (wt-LeuC+L31G-LeuD), 9 (V35A-LeuC+L31G-LeuD), 10 (V35A-LeuC+L31V), 18 (L411V-LeuC+L31G-LeuD), 31 (V35A/L411V-LeuC+L31V-LeuD), 32 (V35A/L411V-LeuC+L31A-LeuD), 39 (W35A/L411G-LeuC+L31G-LeuD), 59 (wt-LeuC+L31V/H88A-LeuD), 61 (wt-LeuC+L31G/H88A-LeuD), 64 (wt-LeuC+L31G/I188S-LeuD), and 115 (V35G/L411V-LeuC+L31A/H88S-LeuD) had 2-341 fold higher activity against 2-HM than the wild type LeuCD (Variant 3). While these various substitutions in LeuC and LeuD increased the activity against 2-HM, they diminished or abolished activity against 2-IPM. Together, the data indicate that these would be significantly less effective than the wild-type enzyme in the earlier cycles of "+1" pathway during the elongation of 2-ketobutyrate, but will be 2 to 341 fold more efficient during later stages of elongation of 2-ketobutyrate to $C_8$-$C_{11}$ 2-ketoacids. Expressing both the wild type LeuCD and variant 1, 5, 6, 9, 10, 18, 31, 32, 39, 59, 61, 64, or 115 would overcome LeuCD related bottleneck during the elongation of 2-ketobutyrate to $C_7$-$C_{11}$ 2-ketoacid and eventually. $C_6$-$C_{10}$ alcohol.

The data shows that the genetically modified LeuCD' enzyme generally operates at a higher catalytic efficiency than that of the wild type enzyme to catalyze, as shown, 2-hexylmalate to form 3-hexylmalate and subsequently 2-ketononanoate. It can also be inferred that it will more efficiently catalyze 2-pentylmalate to form 3-pentylmalate and subsequently 2-ketooctanoate. Finally, it will also likely carry out combinations of these conversions at a higher catalytic efficiency.

As shown in Table 5, several of the LeuCD variant expressing cells produced higher amounts of heptanol and/or octanol than the strain expressing only the wild type LeuCD. This suggests that the LeuCD variants reported here are overcoming the barrier towards the production of >$C_7$ alcohols using the non-natural pathway used here. LeuCD variants 6 and 59 increased heptanol titers, while variants 6, 9, 10, 38, 39, 59, and 61 increased octanol titers compared to those produced by the wild type enzyme. Cells expressing LeuCD variants 6, 9 or 39 produced >6-fold higher amounts of octanol than the WT LeuCD enzyme.

Deposit Information

Microbial strains of E. coli containing the LeuCD variants 38 (V35A/L41 IG-LeuC+L31A-LeuD), E. coli containing the LeuCD variant 39 (W35A/L411G-LeuC+L31G-LeuD), E. coli containing the LeuCD variant 10 (V35A-LeuC+L31V-LeuD). E. coli containing the LeuCD variant 6 (wt-LeuC+L31G-LeuD), E. coli containing the LeuCD variant 59 (wt-LeuC+L31V/H88A-LeuD), E. coli containing the LeuCD variant 9 (V35A-LeuC+L31G-LeuD), and E. coli containing the LeuCD variant 61 (wt-LeuC+L31G/H88A-LeuD), disclosed above and recited in the appended claims, have been made with the American Type Culture Collection (ATCC), 10801 University Boulevard, Manassas, Va. 20110, under the provisions of the Budapest Treaty on the International Recognition of the Deposit of Microorganisms for the Purpose of Patent Procedures. The date of deposit was Sep. 2, 2016 on behalf of Dow Global Technologies. The deposit of 25 vials of each strain were taken from the same deposits maintained by the inventors since prior to the filing date of this application. The deposits are intended to meet all of the requirements of 37 C.F.R. § 1.801-1.809. The deposits will be maintained in the depository for a period of 30 years, or 5 years after the last request, or for the effective life of the patent, whichever is longer, and will be replaced as necessary during that period. Microbial strain of E. coli containing the LeuCD variant 38 (V35A/L411G-LeuC+L31A-LeuD) was deposited on Sep. 2, 2016 at the ATCC (ATCC Patent Deposit Designation: PTA-123472). Microbial strain of E. coli containing the LeuCD variant 39 (W35A/L411G-LeuC+L31G-LeuD) was deposited on Sep. 2, 2016 at the ATCC (ATCC Patent Deposit Designation: PTA-123473). Microbial strain of E. coli containing the LeuCD variant 10 (V35A-LeuC+L31V-LeuD) was deposited on Sep. 6, 2016 at the ATCC (ATCC Patent Deposit Designation: PTA-123474). Microbial strain of E. coli containing the LeuCD variant 6 (wt-LeuC+L31G-LeuD) was deposited on Sep. 6, 2016 at the ATCC (ATCC Patent Deposit Designation: PTA-123475). Microbial strain of E. coli containing the LeuCD variant 59 (wt-LeuC+L31V/H88A-LeuD) was deposited on Sep. 6, 2016 at the ATCC (ATCC Patent Deposit Designation: PTA-123477). Microbial strain of E. coli containing the LeuCD variant 9 (V35A-LeuC+L31G-LeuD) was deposited on Sep. 6, 2016 at the ATCC (ATCC Patent Deposit Designation: PTA-123478). Microbial strain of E. coli containing the LeuCD variant 61 (wt-LeuC+L31G/H88A-LeuD) was deposited on Sep. 6, 2016 at the ATCC (ATCC Patent Deposit Designation: PTA-123479).

The invention claimed is:

1. A microbial organism comprising:
   a genetically modified LeuCD' enzyme complex selected from the group consisting of:
   (i) a combination of a genetically modified LeuC' subunit comprising an amino acid sequence with at least 95% identity to SEQ ID NO: 1 and at least one modification wherein the amino acid at the position corresponding to position 35 of SEQ ID NO: 1 is substituted with alanine and a native LeuD subunit comprising an amino acid sequence with at least 94% identity to SEQ ID NO: 2;
   (ii) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with alanine;
   (iii) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with glycine;
   (iv) a combination of a genetically modified LeuC' subunit comprising an amino acid sequence with at least 95% identity to SEQ ID NO: 1 and at least one modification wherein the amino acid at the position corresponding to position 35 of SEQ ID NO: 1 is substituted with alanine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with glycine;
   (v) a combination of a genetically modified LeuC' subunit comprising an amino acid sequence with at least 95% identity to SEQ ID NO: 1 and at least one modification wherein the amino acid at the position corresponding to position 35 of SEQ ID NO: 1 is substituted with glycine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with valine;
   (vi) a combination of a genetically modified LeuC' subunit comprising an amino acid sequence with at least 95% identity to SEQ ID NO: 1 and at least one modification wherein the amino acid at the position corresponding to position 411 of SEQ ID NO: 1 is substituted with valine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with glycine;
   (vii) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with alanine and the amino acid at the position corresponding to position 411 of SEQ ID NO: 1 is substituted with valine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with valine;
   (viii) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with alanine and the amino acid at the position corresponding to position 411 of SEQ ID NO: 1 is substituted with valine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with alanine;

(ix) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with alanine and the amino acid at the position corresponding to position 411 of SEQ ID NO: 1 is substituted with glycine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with alanine;

(x) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with alanine and the amino acid at the position corresponding to position 411 of SEQ ID NO: 1 is substituted with glycine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with glycine;

(xi) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least the modifications wherein the amino acid at the position corresponding to position 31 of SEQ ID NO: 2 is substituted with valine and the amino acid at the position corresponding to position 88 of SEQ ID NO: 2 is substituted with alanine;

(xii) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least the modifications wherein the amino acid at the position corresponding to position 31 of SEQ ID NO: 2 is substituted with glycine and the amino acid at the position corresponding to position 88 of SEQ ID NO: 2 is substituted with alanine;

(xiii) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least the modifications wherein the amino acid at the position corresponding to position 31 of SEQ ID NO: 2 is substituted with glycine and the amino acid at the position corresponding to position 88 of SEQ ID NO: 2 is substituted with serine; and (xiv) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with glycine and the amino acid at the position corresponding to position 411 of SEQ ID NO: 1 is substituted with valine- and a genetically modified LeuD' subunit comprising an amino acid sequence with at least 94% identity to SEQ ID NO: 2 and at least the modifications wherein the amino acid at the position corresponding to position 31 of SEQ ID NO: 2 is substituted with alanine and the amino acid at the position corresponding to position 88 of SEQ ID NO: 2 is substituted with serine;

wherein the genetically modified LeuCD' enzyme complex has isopropylmalate isomerase activity.

2. A LeuCD' enzyme complex selected from the group consisting of:

(i) a combination of a genetically modified LeuC' subunit comprising an amino acid sequence with at least 95% identity to SEQ ID NO: 1 and at least one modification wherein the amino acid at the position corresponding to position 35 of SEQ ID NO: 1 is substituted with alanine and a native LeuD subunit comprising an amino acid sequence with at least 94% identity to SEQ ID NO: 2;

(ii) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with alanine;

(iii) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with glycine;

(iv) a combination of a genetically modified LeuC' subunit comprising an amino acid sequence with at least 95% identity to SEQ ID NO: 1 and at least one modification wherein the amino acid at the position corresponding to position 35 of SEQ ID NO: 1 is substituted with alanine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with glycine;

(v) a combination of a genetically modified LeuC' subunit comprising an amino acid sequence with at least 95% identity to SEQ ID NO: 1 and at least one modification wherein the amino acid at the position corresponding to position 35 of SEQ ID NO: 1 is substituted with glycine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with valine;

(vi) a combination of a genetically modified LeuC' subunit comprising an amino acid sequence with at least 95% identity to SEQ ID NO: 1 and at least one modification wherein the amino acid at the position corresponding to position 411 of SEQ ID NO: 1 is substituted with valine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with glycine;

(vii) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with alanine and the amino acid at the position corresponding to position 411 of SEQ ID NO: 1 is substituted with valine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with valine;

(viii) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with alanine and the amino acid at the position corresponding to position 411 of SEQ ID NO: 1 is substituted with valine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with alanine;

(ix) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with alanine and the amino acid at the position corresponding to position 411 of SEQ ID NO: 1 is substituted with glycine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with alanine;

(x) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with alanine and the amino acid at the position corresponding to position 411 of SEQ ID NO: 1 is substituted with glycine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with glycine;

(xi) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least the modifications wherein the amino acid at the position corresponding to position 31 of SEQ ID NO: 2 is substituted with valine and the amino acid at the position corresponding to position 88 of SEQ ID NO: 2 is substituted with alanine;

(xii) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least the modifications wherein the amino acid at the position corresponding to position 31 of SEQ ID NO: 2 is substituted with glycine and the amino acid at the position corresponding to position 88 of SEQ ID NO: 2 is substituted with alanine;

(xiii) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least the modifications wherein the amino acid at the position corresponding to position 31 of SEQ ID NO: 2 is substituted with glycine and the amino acid at the position corresponding to position 88 of SEQ ID NO: 2 is substituted with serine; and (xiv) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with glycine and the amino acid at the position corresponding to position 411 of SEQ ID NO: 1 is substituted with valine and a genetically modified LeuD' subunit comprising an amino acid sequence with at least 94% identity to SEQ ID NO: 2 and at least the modifications wherein the amino acid at the position corresponding to position 31 of SEQ ID NO: 2 is substituted with alanine and the amino acid at the position corresponding to position 88 of SEQ ID NO: 2 is substituted with serine;

wherein the genetically modified LeuCD' enzyme complex has isopropylmalate isomerase activity.

3. A protein complex having isopropylmalate isomerase activity, where said complex comprises:
  (i) a polypeptide that comprises all of SEQ ID NO: 1 except for one or more amino acid substitutions at positions corresponding to positions of SEQ ID NO: 1 selected from positions 35 and 411, wherein the amino acid at the position corresponding to position 35 of the polypeptide of SEQ ID NO:1 is replaced with glycine or alanine, and the amino acid at the position corresponding to position 411 of the polypeptide of SEQ ID NO:1 is replaced with valine or glycine, and
  (ii) a polypeptide that comprises all of SEQ ID NO: 2 except for one or more amino acid substitutions at positions corresponding to positions of SEQ ID NO: 2 selected from positions 31 and 88, wherein the amino acid at the position corresponding to position 31 of the polypeptide of SEQ ID NO: 2 is replaced with alanine, valine, or glycine, and wherein the amino acid at the positon corresponding to position 88 of the polypeptide of SEQ ID NO: 2 is replaced with alanine gr serine.

4. A process for preparing a $C_7$-$C_{11}$ 2-ketoacid, the process comprising providing at least one of a $C_4$-$C_{10}$ 2-ketoacid substrate with:
  (A) at least one isopropylmalate synthase enzyme having isopropylmalate synthase activity;
  (B) at least one isopropylmalate dehydrogenase enzyme having isopropylmalate dehydrogenase activity; and
  (C) at least one genetically modified LeuCD' enzyme complex selected from the group consisting of:
    (i) a combination of a genetically modified LeuC' subunit comprising an amino acid sequence with at least 95% identity to SEQ ID NO: 1 and at least one modification wherein the amino acid at the position corresponding to position 35 of SEQ ID NO: 1 is substituted with alanine and a native LeuD subunit comprising an amino acid sequence with at least 94% identity to SEQ ID NO: 2;

(ii) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with alanine;

(iii) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with glycine;

(iv) a combination of a genetically modified LeuC' subunit comprising an amino acid sequence with at least 95% identity to SEQ ID NO: 1 and at least one modification wherein the amino acid at the position corresponding to position 35 of SEQ ID NO: 1 is substituted with alanine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with glycine;

(v) a combination of a genetically modified LeuC' subunit comprising an amino acid sequence with at least 95% identity to SEQ ID NO: 1 and at least one modification wherein the amino acid at the position corresponding to position 35 of SEQ ID NO: 1 is substituted with glycine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with valine;

(vi) a combination of a genetically modified LeuC' subunit comprising an amino acid sequence with at least 95% identity to SEQ ID NO: 1 and at least one modification wherein the amino acid at the position corresponding to position 411 of SEQ ID NO: 1 is substituted with valine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with glycine;

(vii) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with alanine and the amino acid at the position corresponding to position 411 of SEQ ID NO: 1 is substituted with valine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with valine;

(viii) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with alanine and the amino acid at the position corresponding to position 411 of SEQ ID NO: 1 is substituted with valine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with alanine;

(ix) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with alanine and the amino acid at the position corresponding to position 411 of SEQ ID NO: 1 is substituted with glycine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with alanine;

(x) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with alanine and the amino acid at the position corresponding to position 411 of SEQ ID NO: 1 is substituted with glycine and a genetically modified LeuD' subunit comprising an amino acid sequence with at least 94% identity to SEQ ID NO: 2 and at least one modification wherein the amino acid at the position corresponding to position 31 of SEQ ID NO: 2 is substituted with glycine;

(xi) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least the modifications wherein the amino acid at the position corresponding to position 31 of SEQ ID NO: 2 is substituted with valine and the amino acid at the position corresponding to position 88 of SEQ ID NO: 2 is substituted with alanine;

(xii) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least the modifications wherein the amino acid at the position corresponding to position 31 of SEQ ID NO: 2 is substituted with glycine and the amino acid at the position corresponding to position 88 of SEQ ID NO: 2 is substituted with alanine;

(xiii) a combination of a native LeuC subunit comprising an amino acid sequence with at least 95% identity to SEQ ID NO: 1 and a genetically modified LeuD' subunit comprising an amino acid sequence with at least 94% identity to SEQ ID NO: 2 and at least the modifications wherein the amino acid at the position corresponding to position 31 of SEQ ID NO: 2 is substituted with glycine and the amino acid at the position corresponding to position 88 of SEQ ID NO: 2 is substituted with serine; and (xiv) a combination of a genetically modified LeuC' subunit comprising an amino acid sequence with at least 95% identity to SEQ ID NO: 1 and at least the modifications wherein the amino acid at the position corresponding to position 35 of SEQ ID NO: 1 is substituted with glycine and the amino acid at the position corresponding to position 411 of SEQ ID NO: 1 is substituted with valine and a genetically modified LeuD' subunit comprising an amino acid sequence with at least 94% identity to SEQ ID NO: 2 and at least the modifications wherein the amino acid at the position corresponding to position 31 of SEQ ID NO: 2 is substituted with alanine and the amino acid at the position corresponding to position 88 of SEQ ID NO: 2 is substituted with serine;

under conditions that the at least one of the $C_4$-$C_{10}$ 2-ketoacid substrate is converted to the $C_7$-$C_{11}$ 2-ketoacid; wherein the at least one genetically modified LeuCD enzyme complex has isopropylmalate isomerase activity; and wherein the conversion of the at least one of the $C_4$-$C_{10}$ 2-ketoacid substrate to the $C_7$-$C_{11}$ 2-ketoacid occurs via one or more biochemical reactions.

5. The process according to claim 4, wherein the at least one of the $C_4$-$C_{10}$ 2-ketoacid substrate comprises 2-ketobutyrate.

6. The process according to claim 4, wherein the at least one of the $C_4$-$C_{10}$ 2-ketoacid substrate comprises 2-ketoisovalerate.

7. The process according to claim 4, wherein the at least one of the $C_4$-$C_{10}$ 2-ketoacid substrate comprises 2-methyl-2-ketopentanoate.

* * * * *